United States Patent
Fritsch

(10) Patent No.: US 11,057,722 B2
(45) Date of Patent: *Jul. 6, 2021

(54) HEARING AID FOR PEOPLE HAVING ASYMMETRIC HEARING LOSS

(71) Applicant: EAR TECH LLC, Indianapolis, IN (US)

(72) Inventor: Michael H Fritsch, Indianapolis, IN (US)

(73) Assignee: Ear Tech, LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/740,414

(22) Filed: Jan. 11, 2020

(65) Prior Publication Data

US 2020/0236475 A1 Jul. 23, 2020

Related U.S. Application Data

(63) Continuation-in-part of application No. 16/673,788, filed on Nov. 4, 2019, now abandoned, which is a
(Continued)

(51) Int. Cl.
*H04R 25/00* (2006.01)
*G08B 6/00* (2006.01)
*G08B 5/36* (2006.01)

(52) U.S. Cl.
CPC .......... *H04R 25/552* (2013.01); *G08B 5/36* (2013.01); *G08B 6/00* (2013.01); *H04R 25/505* (2013.01); *H04R 25/606* (2013.01)

(58) Field of Classification Search
CPC ...... H04R 25/00; H04R 25/55; H04R 25/558; H04R 2225/49; H04R 2460/01
(Continued)

(56) References Cited

U.S. PATENT DOCUMENTS 5,029,216 A 7/1991 Jhabvala et al.
5,991,419 A 11/1999 Brander
(Continued)

OTHER PUBLICATIONS

Hol, Myrthe K.S., Snik, Ad F.M., Kunst, Sylvia J., and Cremers, Cor W.R.J. Pilot Study on the effectiveness of the conventional DROS, the transcranial CROS and the BAHA transcranial CROS in adults with unilateral inner ear deafness. European Archives of Oto-Thino-Laryngology. Nov. 2009.
(Continued)

*Primary Examiner* — Suhan Ni
(74) *Attorney, Agent, or Firm* — Indiano Law Group LLC; E. Victor Indiano; John T. Woods, III

(57) ABSTRACT

A hearing aid is provided for use with a user having a first and second ears disposed on first and second body sides. The hearing aid apparatus is configured for enabling the user to hear sounds that originate from a plurality of directions and includes a first hearing aid member placeable on a user's first body side. The first hearing aid member includes a first transducer for receiving sounds that would be received by the user's first ear and converting those received sounds into first transmittable electrical signals. A second hearing aid member is placeable on the user's second body side and is preferably a cochlear implant device including an electrode array positionable within a cochlea of a user. The cochlear implant device includes a second transducer for receiving sounds that would be received by the user's second ear, and converting the sounds into second electrical signals; and also includes a receiver for receiving the first transmittable electrical signals, and a first signal processor for processing the second electrical signals and first transmittable electrical signals into signals configured for being received by the cochlea of user's second ear for facilitating the hearing of sounds that would be received by both of the user's first and second ears.

35 Claims, 19 Drawing Sheets

Related U.S. Application Data continuation-in-part of application No. 15/268,555, filed on Sep. 17, 2016, now Pat. No. 10,484,802.

(60) Provisional application No. 62/220,285, filed on Sep. 18, 2015.

(58) Field of Classification Search
USPC .................................. 381/312–313, 315–317
See application file for complete search history.

(56) References Cited

U.S. PATENT DOCUMENTS

| | | |
|---|---|---|
| 6,549,633 B1 | 4/2003 | Westermann |
| 7,650,194 B2 | 1/2010 | Fritsch et al. |
| 7,953,237 B2 | 5/2011 | Sporer |
| 8,121,321 B2 | 2/2012 | Iwano |
| 8,208,642 B2 | 6/2012 | Edwards |
| 8,805,546 B2 | 8/2014 | Dadd et al. |
| 8,809,348 B2 | 12/2014 | Fritsch et al. |
| 2006/0093172 A1 | 5/2006 | Ludvigsen et al. |
| 2006/0198529 A1 | 9/2006 | Kjems et al. |
| 2007/0005117 A1 | 1/2007 | Fritsch et al. |
| 2007/0149261 A1 | 6/2007 | Huddart |
| 2007/0225776 A1 | 9/2007 | Fritsch et al. |
| 2008/0045859 A1 | 2/2008 | Fritsch et al. |
| 2008/0273727 A1 | 11/2008 | Hagen et al. |
| 2011/0130696 A1 | 6/2011 | Fritsch et al. |
| 2011/0245891 A1 | 10/2011 | Fritsch et al. |
| 2014/0270187 A1 | 9/2014 | Hall et al. |
| 2017/0085998 A1 | 3/2017 | Fritsch |
| 2018/0220239 A1 | 8/2018 | Keady et al. |
| 2019/0239006 A1 | 8/2019 | Petersen et al. |

OTHER PUBLICATIONS

Valente, Michael, Valente, Maureen, and Mispagel, Karen. Fitting Options for Adult Patients with Single Sided Deafness (SSD). Audiologyonline. https://www.audiologyonline.com/artices/fitting-options-for-adult-patients-980. Aug. 14, 2006.
WIPO, PCT Search Report, WrittenOpinion of the ISA-US, dated Mar. 30, 2021.

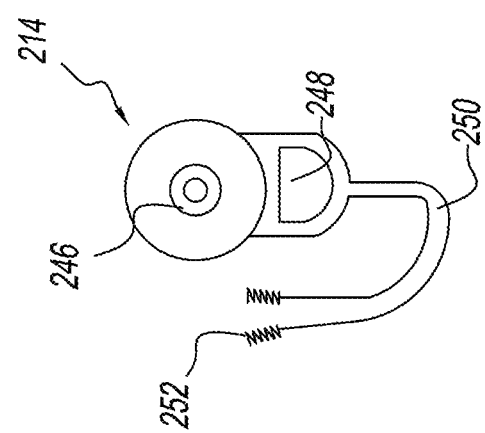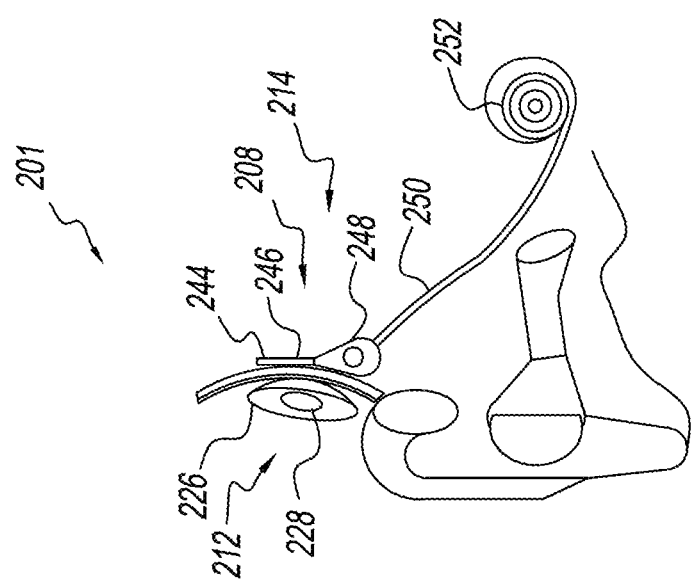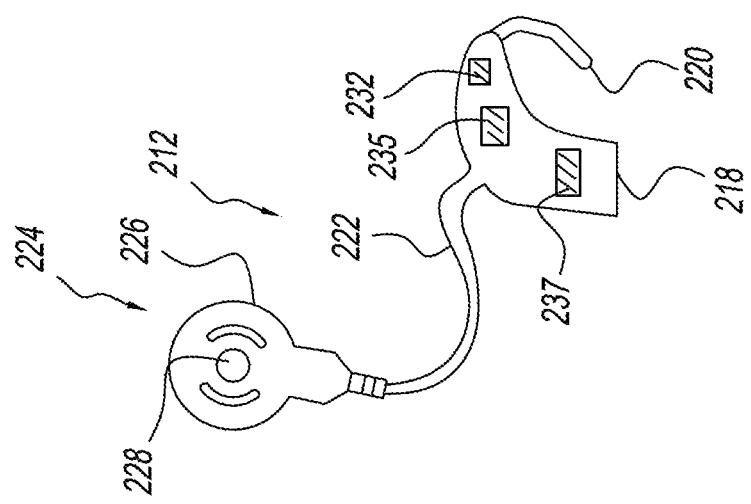

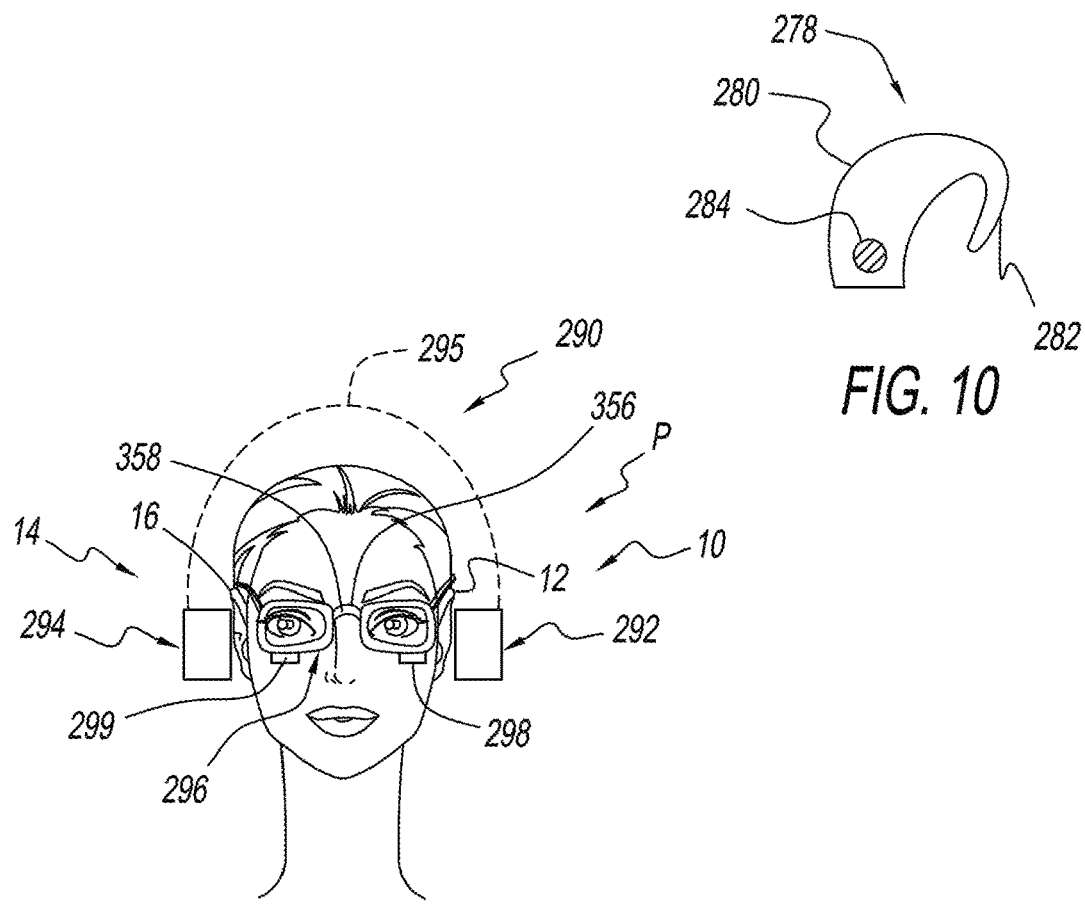
FIG. 10
FIG. 11
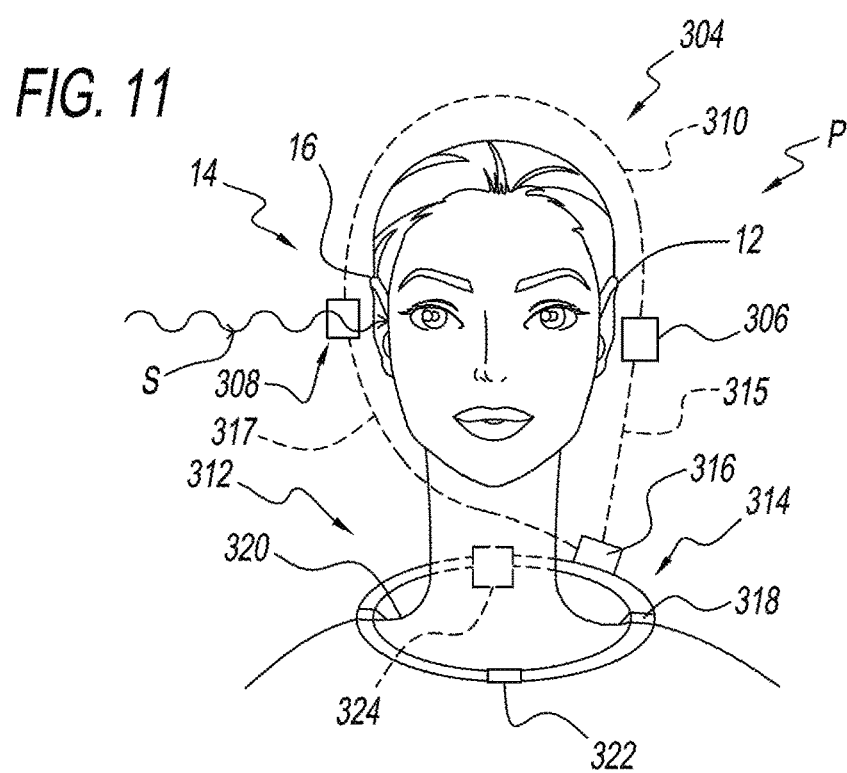
FIG. 12

HEARING AID FOR PEOPLE HAVING ASYMMETRIC HEARING LOSS

BENEFIT OF PRIORITY

The instant application is a continuation-in-part of Michael H. Fritsch U.S. patent application Ser. No. 16/673,788, which was filed on 4 Nov. 2019, which itself is a continuation-in-part of Michael H. Fritsch U.S. patent application Ser. No. 15/268,555 which was filed on 17 Sep. 2016 for HEARING AID FOR PEOPLE HAVING ASYMMETRIC HEARING LOSS; which itself claims benefit of priority to Michael H. Fritsch, U.S. Provisional Patent Application No. 62/220,285 that was filed on 17 Sep. 2015 for a HEARING AID FOR PEOPLE HAVING ASYMMETRIC HEARING LOSS, all of which patent applications are incorporated by reference herein in their entireties

I. TECHNICAL FIELD OF THE INVENTION

The present invention relates to devices for aiding in hearing, including external hearing aids, BAHA devices, cochlear implant devices, and other hearing-related devices, and more particularly, to a device for aiding in hearing that is especially useful for people with an asymmetric hearing loss. The device can comprise a standalone hearing aid, or can comprise a device useable in conjunction with an external hearing aid, or cochlear implant. Unless used in a specific reference to an external hearing aid, the term hearing aid as used in this document should be interpreted broadly enough to encompass all forms of devices that enable a user to hear better.

BACKGROUND OF THE INVENTION

Hearing loss is not uncommon in persons, who are either born with a hearing loss or who develop a hearing loss later in life. When a hearing loss develops, the hearing loss is not always equal bilaterally. In particular, it is not unusual that one ear will have less hearing loss than the other, and therefore have better auditory acuity than the relatively more hearing-impaired other ear. For example, someone may have a 70% hearing loss in their left ear, but only a 30% hearing loss in their right ear.

Also, unusual cases exist where a tumor has destroyed or damaged one ear, although the person has an undamaged, normal opposite ear which results in an asymmetric auditory acuity between the two ears. In certain instances, the hearing loss in one ear can be very profound, so that the person for example, has an auditory acuity in a bad ear that may be only 10% to 20% of the auditory acuity of a "normal ear."

For the sake of consistency, the application will assume that the user's first or left ear is her "bad" ear and that the person's second right ear is her "good" ear. It will be appreciated that the choice of "first and left" for the bad ear is and "right and second" for the good ear is a purely arbitrary convention, and is not to be taken as any sort of limitation. It will also be noted that as used herein, a "good" ear is one with a greater auditory acuity than the "bad" ear, and that "good" and "bad" are relative and comparative terms, and not absolutes. It will further be appreciated that the difference between the auditory acuity of the good ear and the bad ear is highly variable between a condition where the difference in auditory acuity between the two ears is unnoticeable to the user; and an opposite extreme where the good ear has normal or above normal auditory acuity, and the bad ear has no auditory acuity. Normally an asymmetric hearing loss is treated when a person obtains hearing aids, and the asymmetric hearing loss is diagnosed by the practitioner.

The usual manner in which an asymmetric hearing loss is treated is to place a hearing aid in each of the ears. Often, the hearing aid placed in the "bad" ear can be adjusted so that it amplifies the sound to a greater degree than the hearing aid placed in the "good" ear. Unfortunately, some hearing losses are so profound that a normal or approximately symmetric hearing condition cannot be restored even with an amplification adjusted hearing aid. For example, even with a hearing aid, a user may have an effective hearing acuity of only thirty percent (30%) in his bad ear whereas his good ear has a corrected hearing ability to within normal limits. In this application, the term "profoundly asymmetric hearing loss" will be used to identify a condition where the hearing loss of an ear is sufficiently great that sound amplification devices, such as hearing aids, will not restore useable hearing acuity to that ear. Profoundly asymmetric hearing loss also includes a condition wherein the hearing of the bad ear cannot be restored without resorting to an invasively placed sound amplification device such as a cochlear implant.

Users experience difficulty with hearing in such cases where the ears cannot be corrected equally to provide symmetric hearing. In particular, a user often will hear accurate, clear sound information out of her good ear, but garbled information out of her bad ear. This combination of garbled and clear sound information becomes very distracting to the user. In many cases, the user will treat the distraction by removing the hearing aid from the bad ear, and rely solely on the good ear to provide all of her hearing, as this is more pleasing aesthetically and is less distracting than having his hearing aid in her bad ear providing garbled sound information.

However, using only a single hearing aid has drawbacks. In particular, the user loses the sense of directionality that he obtains from having bilateral hearing. For example, if the user hears everything from his right ear and has no hearing out of this left ear, he cannot easily determine the direction from which a particular sound originates.

A further problem experienced by users having an asymmetric hearing loss is that they are often unable to hear sounds that originate from the side of the user on which the bad ear is located. As such, a user sitting at a table might be able to very easily understand a conversation spoken by people sitting on his good ear side, but may not be able to hear anything from those sitting on his bad ear side. This inability to hear well on one side forces the user to turn her head on a frequent basis so that her good ear is better positioned to pick up the sound originating from the user's bad ear side. This frequent head turning can also be dangerous when driving a motor vehicle, or awkward such as when trying to write notes and turning one's head often to be sure that you have heard the auditory information on which the notes are being taken.

Those with asymmetric hearing loss often try to find ways of compensating for their inability to hear well on one side. For example, persons having hearing in only one ear will often try to choose a place at a table where all of the other people at the table are seated on their "good ear side". Another compensation technique is for the user to sit at the end of the table facing all the other persons, so that the "bad ear side" is positioned so that no one is sitting directly on the bad ear side.

Known technological fixes exist for aiding in overcoming these issues. These methods include the use of "CROS"

hearing aids, "BICROS" hearing aids, and bone-anchored hearing aids ("BAHA" hearing aids).

A CROS hearing aid is a type of hearing aid that is used to treat unilateral hearing loss. A CROS hearing aids often include a microphone placed on the user's bad ear side that receives sound from the user's bad ear side and transmits the sound to the good ear with better hearing. Many systems use a wireless transmitter to transmit electrical signals from the bad ear positioned hearing aid to the good ear positioned hearing aid.

BAHA and Trans-cranial CROS systems use the conductivity of the skull to transmit sounds. See, e.g. Wikipedia, CROS *Hearing Aid*, https:/en.wikipedia,org/wiki/CROS-_hearing-aid; See also Myrthe K. S. Hol; Sylvia J. W. Kunst et al, "Pilot Study on the Effectiveness of the Conventional CROS, the Transcranial CROSS and the BAHA Transcranial CROS in Adults with Unilateral Inner Ear Deafness", *European Archives of Oto-Rhino-Laryngology*, 2010, June 267 (6), 889-896 (2009, Nov. 11).

A BICROS hearing aid system is primarily employed on users who have little or no hearing on one side, with some hearing loss in their good ear. A BICROS system works similarly to a CROS system, except that the device on the good side is usually a fully capable hearing aid for receiving and amplifying sounds on the good ear side and is also capable of receiving the sound transmitted from the CROS hearing aid on the bad side.

A BAHA (Bone Anchored Hearing Aid) is a hearing aid that is placed on the side of the bad ear, and transfers sound through bone conduction and stimulates the cochlea of the good ear. This system is designed to transmit sound from the bad side to the good hearing side to result in a sensation of hearing from the deaf ear. See www.umm.edu/PROGRAMS/HEARING/SERVICES/BONE-ANCHORED-DEVICE#UNILATERAL, University of Maryland Medical Center.

A BAHA hearing aid typically employs a biocompatible screw that is affixed into the skull behind the bad ear. The screw top is a coupling intended for a vibrating bone conductor hearing aid. The hearing aid vibrations are transmitted through the screw and into the skull bone and are transmitted through the skull to the opposite good ear. This is similar to a tuning fork placed on a bone so that the vibrations from the tuning fork vibrate the surfaces it touches and thereby transmits sound vibrations through the skull and to the ear.

The CROS, BICROS hearing aid and the Bone Anchored Hearing Aid provide significant advantages to the user, as they enable the user to hear information from both sides of his head. However, although they provide the hearing information to the user, known CROS, BICROS and BAHA hearing aids are not very effective in providing the user with a sense of directionality. In essence, the user is hearing the information in "monoraul", and does not enjoy the stereophonic sound that a person with two normally functioning ears enjoys. Because of this monoraul hearing, the user can hear the information, but cannot determine whether the sounds that he is hearing are originating from his bad hearing side or good hearing side.

Therefore, one object of the present invention is to provide a device that enables the user to have better directionality as to the source of sounds and speakers' voices.

III. SUMMARY OF THE INVENTION

In accordance with the present invention, a hearing device apparatus is provided for use with a user having a first ear and a first body side on which the first ear is disposed, and a second ear and a second body side on which the second ear is disposed. The hearing aid apparatus is configured for enabling the user to hear sounds that originate from a plurality of directions. The hearing aid apparatus comprises a first hearing aid member placeable on a user's body on the same side of the user's body as the first ear. The first hearing aid member includes a first transducer for receiving sounds that would be received by the user's first ear and converting those received sounds into first transmittable electrical signals.

A second hearing aid member is placeable on the user's second body side. The second hearing aid member comprises a cochlear implant device including an electrode array positionable within a cochlea of a user. The cochlear implant device includes a second transducer for receiving sounds that would be received by the user's second ear and converting the received sounds into second electrical signals. The cochlear implant device also includes receiver for receiving the first transmittable electrical signals, and a first signal processor for processing the second electrical signals and first transmittable electrical signals into signals configured for being received by the cochlea of user's second ear for facilitating the hearing of sounds that would be received by both of the user's first and second ears. The only functionally hearable sound signals received by the user's ear are generated through the second hearing aid member.

In a preferred embodiment, the hearing aid also includes a signal alteration processor for altering one of the first transmittable electrical signal and second electrical signal so that the user can hear differences between sounds received by the first hearing aid member and sounds received by the second hearing aid member. This permits the user to distinguish between sounds received by the first hearing aid member and sounds received by the second hearing aid member, thereby aiding the user in achieving a sense of the direction of origin of the sounds being output into the second ear.

Most preferably, an alteration signal processes a signal of the at least one of the first and second electrical signals to alter the signal by at least one of changing its pitch, inducing an echo, delaying the signal, filtering the signal, adding a chorus effect, attenuating different frequency bands, resonating the signal, adding an artifact signal, adding an artifact to the signal, changing the strength of the signal to alter its volume, and modulating the signal.

One of the features of the present invention is that a signal processor is provided that can alter one of the first and second signals, so that the altered one of the first and second signals produces a sound that is auditorily distinguishable from the unaltered one of the first and second signals. This feature has the advantage of providing the user with some means for determining directionality of the signal. For example, if the user's "bad ear" is the user's first ear, and the user's "good ear" (or at least relatively better ear) is the user's second ear, the device is designed to receive sound from the first side of the user, and then alter the sound so that the sound has a different tonal quality than the sound of the second signal.

Hopefully, the user will learn to recognize this difference in tonal quality, so that the user can help to make a determination based on this difference in tonal quality as to whether the sound is originating from the user's first ear side, or the user's second ear side. By so doing this, a user who has only one good ear, or who more particularly only has one ear that is capable of receiving relatively high fidelity sounds, and as such, is relegated to have something of a "monoraul" hearing will be able to have something that approximates a "stereophonic" hearing, that will help the user to provide him with some sound directionality.

In another embodiment, sound information can be transferred between the user's bad side ear" and the user's "good side ear" through the use of a bone anchored hearing aid. Such a bone anchored hearing aid vibrates or induces vibrations into the bone structure of the user's head, so that the vibrations can be transmitted from the user's bad side to the user's good side, and then converted into sound energy, so that the user can also obtain the illusion of stereo phonic, bi-directional hearing.

These and other features of the present invention will become apparent to those skilled in the art, upon a review of the detailed description, claims and drawings set forth below.

IV. BRIEF DESCRIPTION OF THE DRAWINGS

Figure 6:
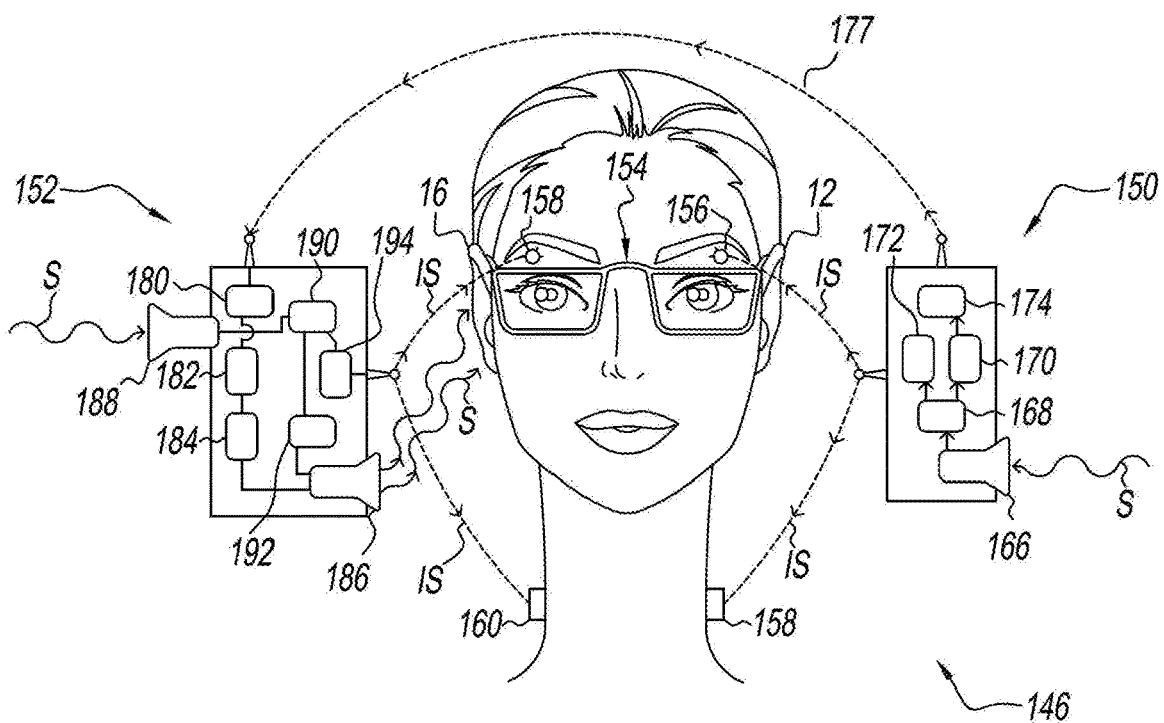
Figure 7:
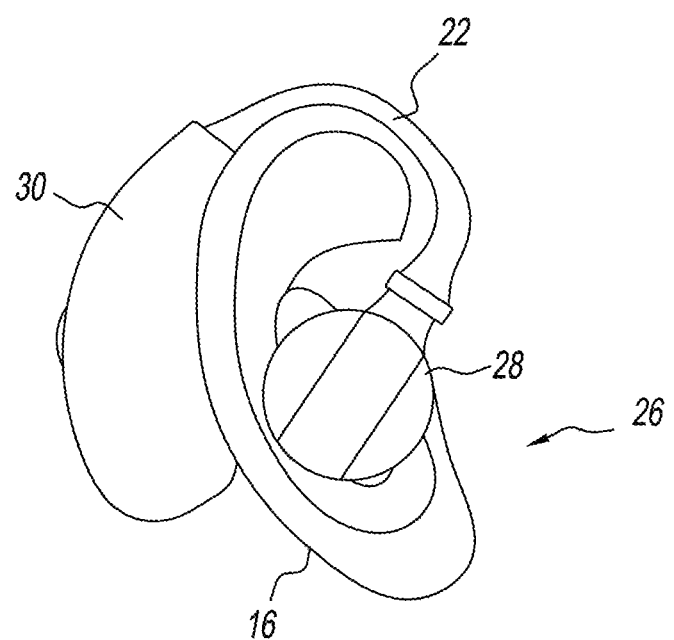

FIG. 6 is an alternate embodiment hearing aid system of the present invention, that can incorporate any of the hearing aid systems of the present invention, but to which is added both a visual and a vibratory direction indicator to help the user identify sound direction; and FIG. 7 is a schematic view of a prior art hearing aid, to show the type of packaging in which the hearing aid system of the present invention may be placed.

Figure 8C:
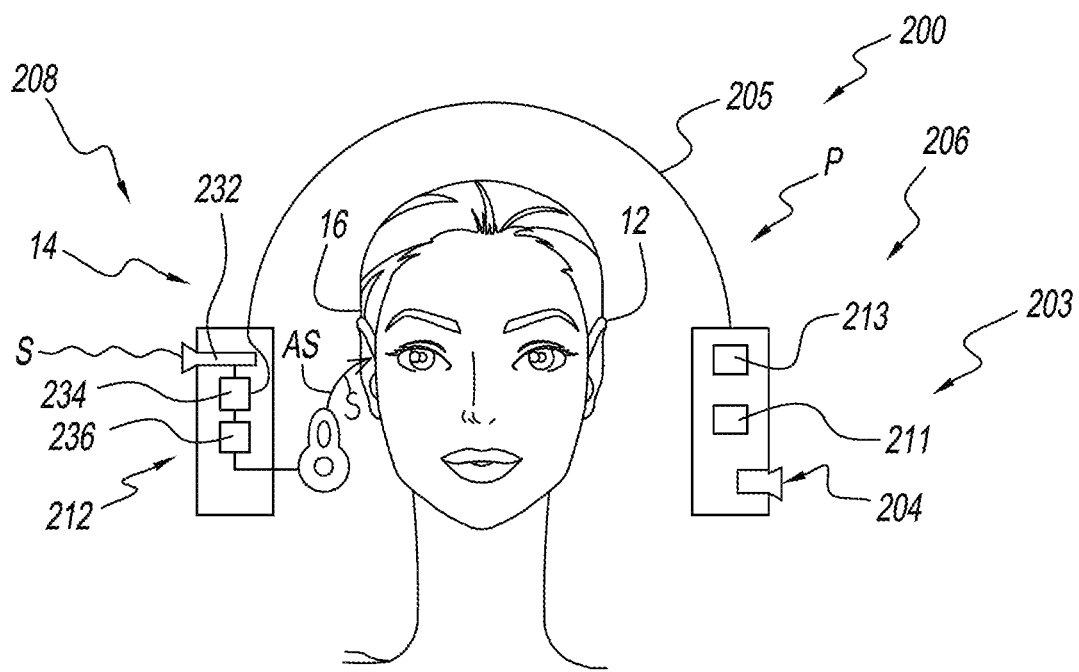
Figure 9:
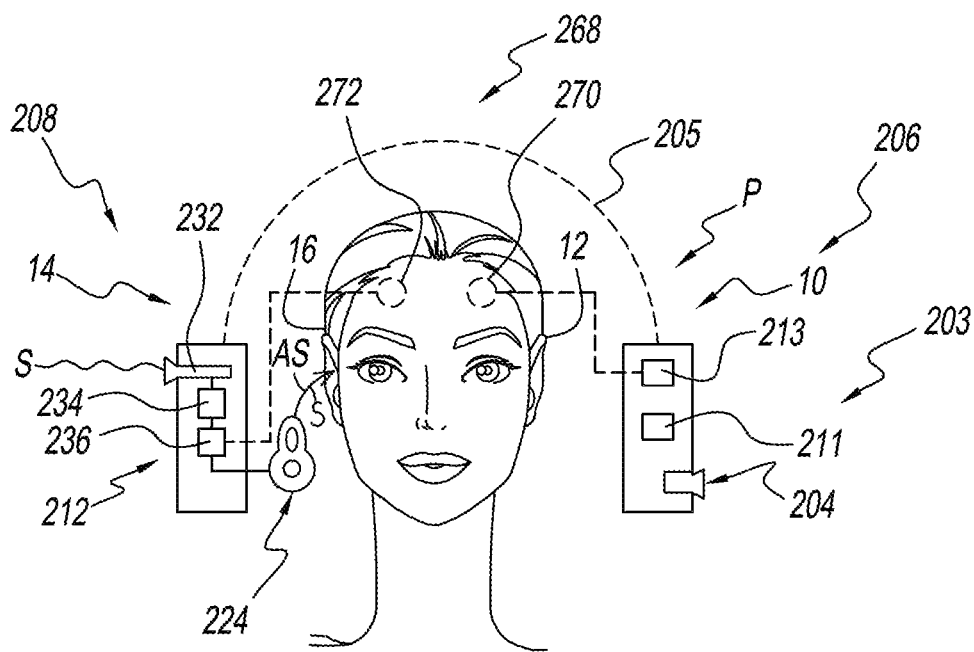

FIG. 8 is a side view of an external component of a cochlear implant type hearing aid system;

FIG. 8A is a top view of the internal component of a cochlear implant system;

FIG. 8B is a sectional, partly schematic view of a cochlear implant system that is installed within a person, to include an external component of FIG. 8, and an internal component of FIG. 8A;

FIG. 8C is a schematic version of an alternate embodiment of an asymmetrical hearing aid apparatus of the present invention that incorporates the cochlear implant system of FIGS. 8-8B;

FIG. 9 is a schematic view of another alternate embodiment of a cochlear implant system that employs a non-audible indicia in lieu of, or in addition to, the audible indicia.

Figure 13:
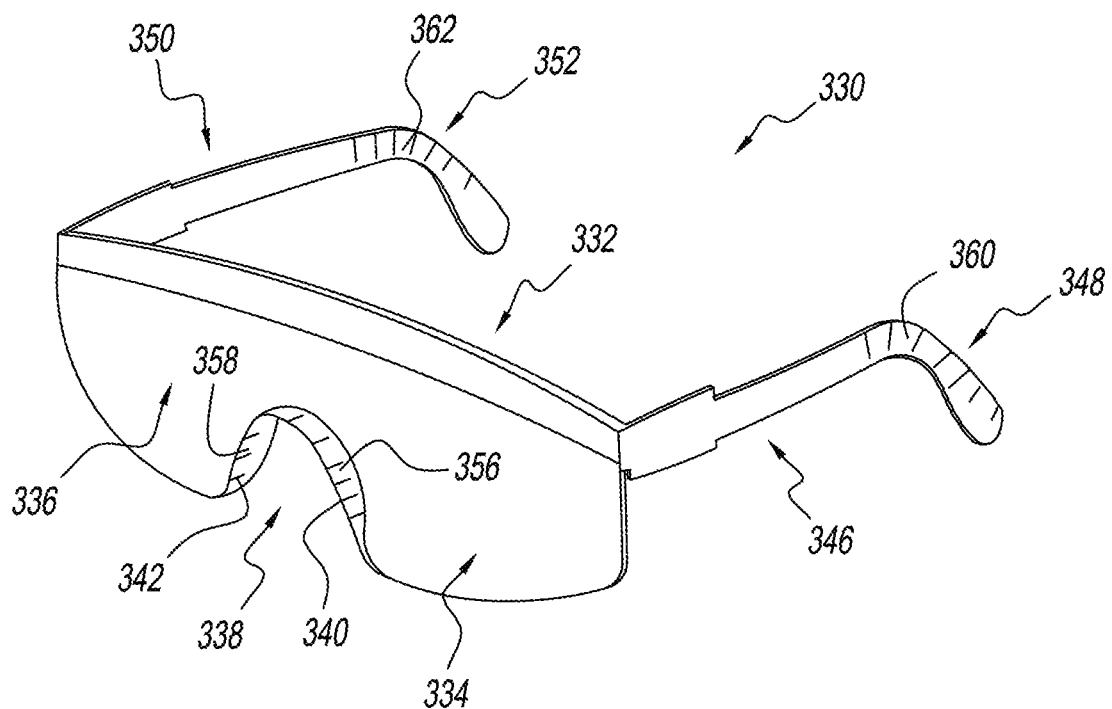
Figure 14:
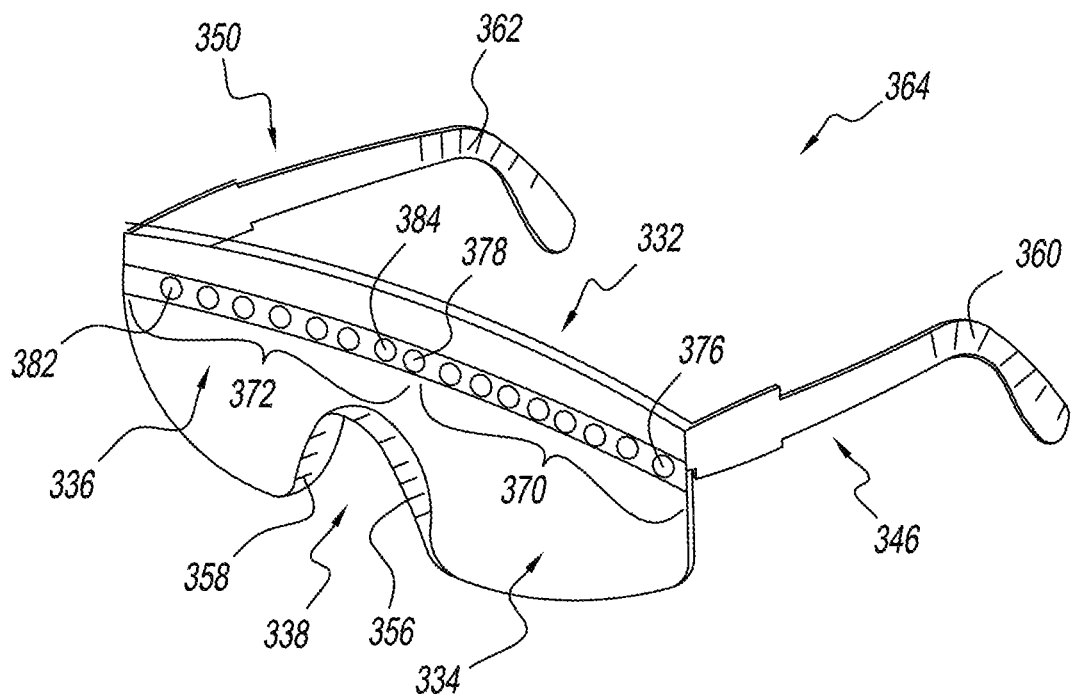
Figure 15:
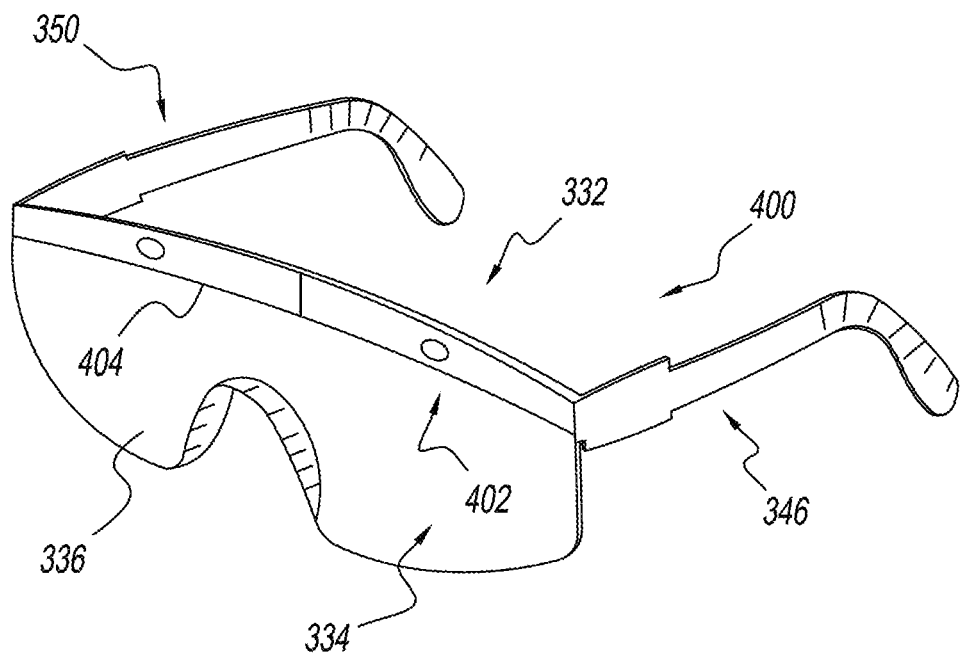
Figure 16:
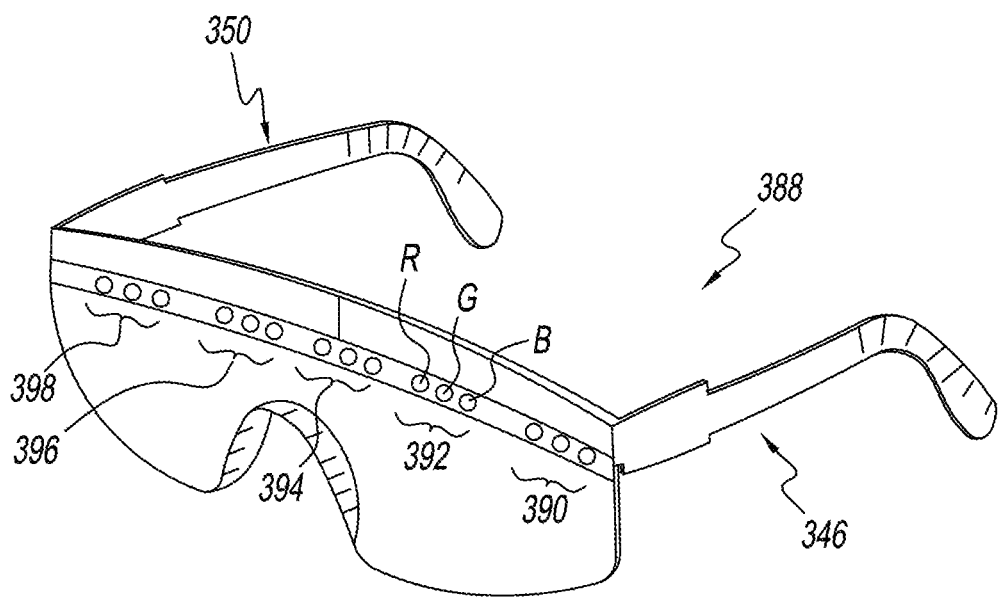
Figure 17:
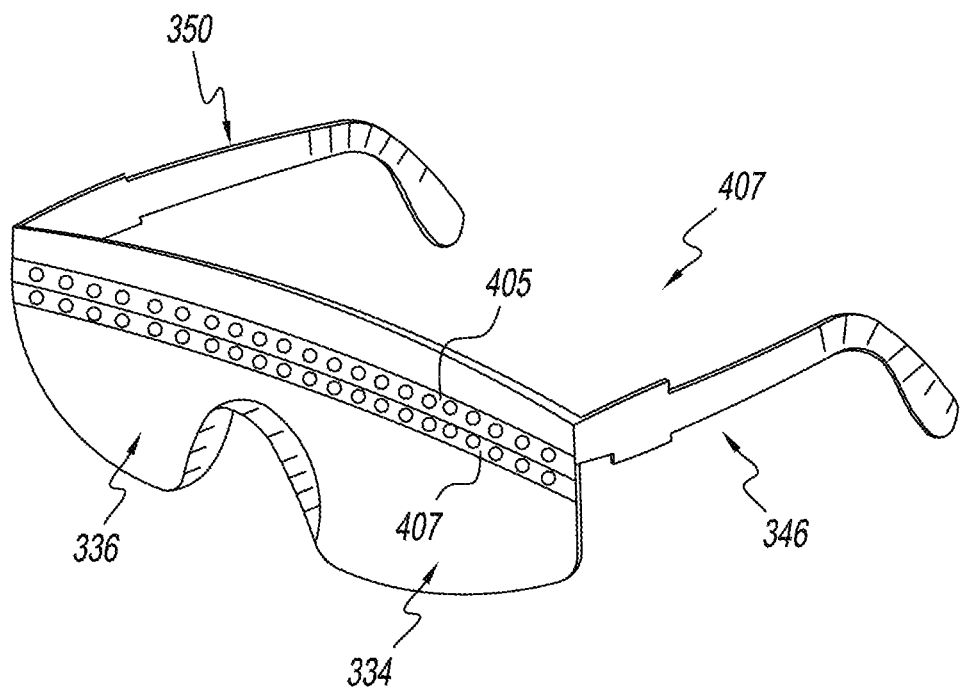
Figure 18:
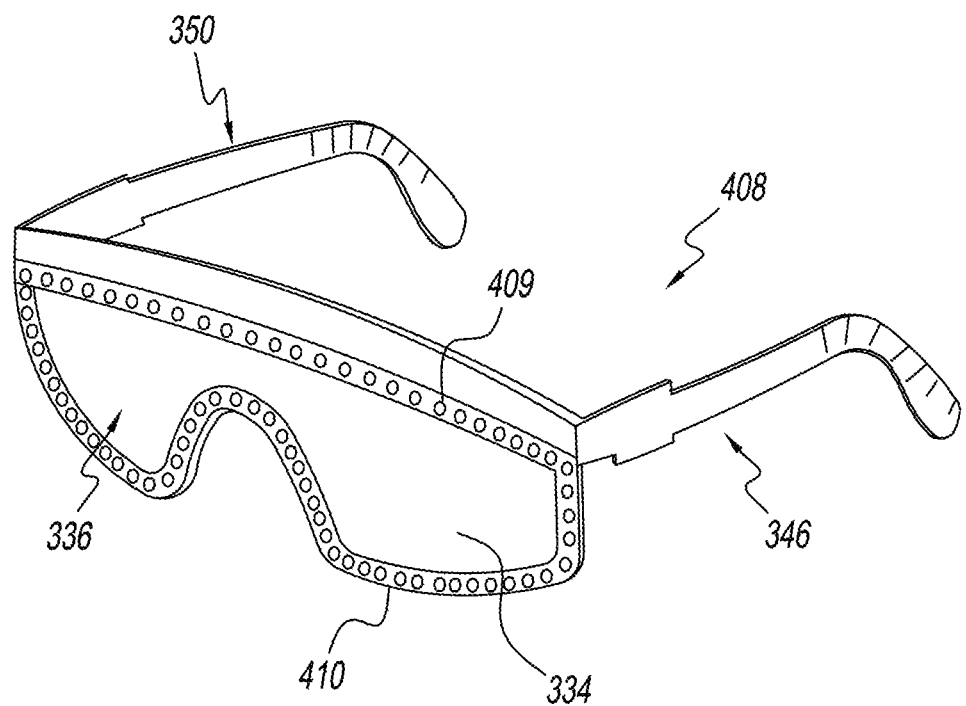
Figure 19:
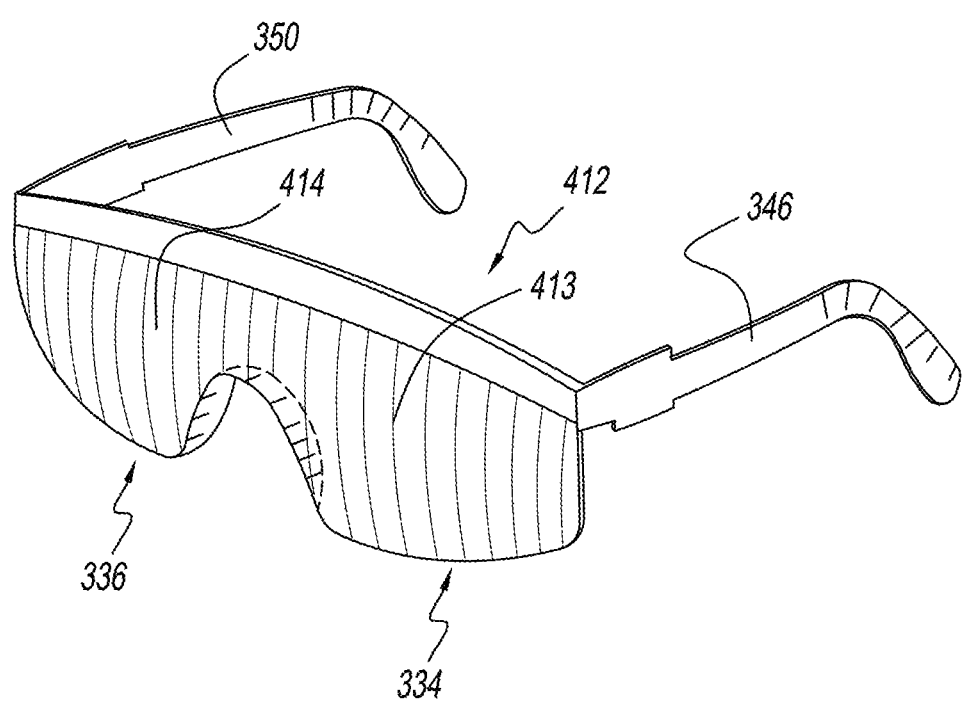
Figures 19A, 19B:
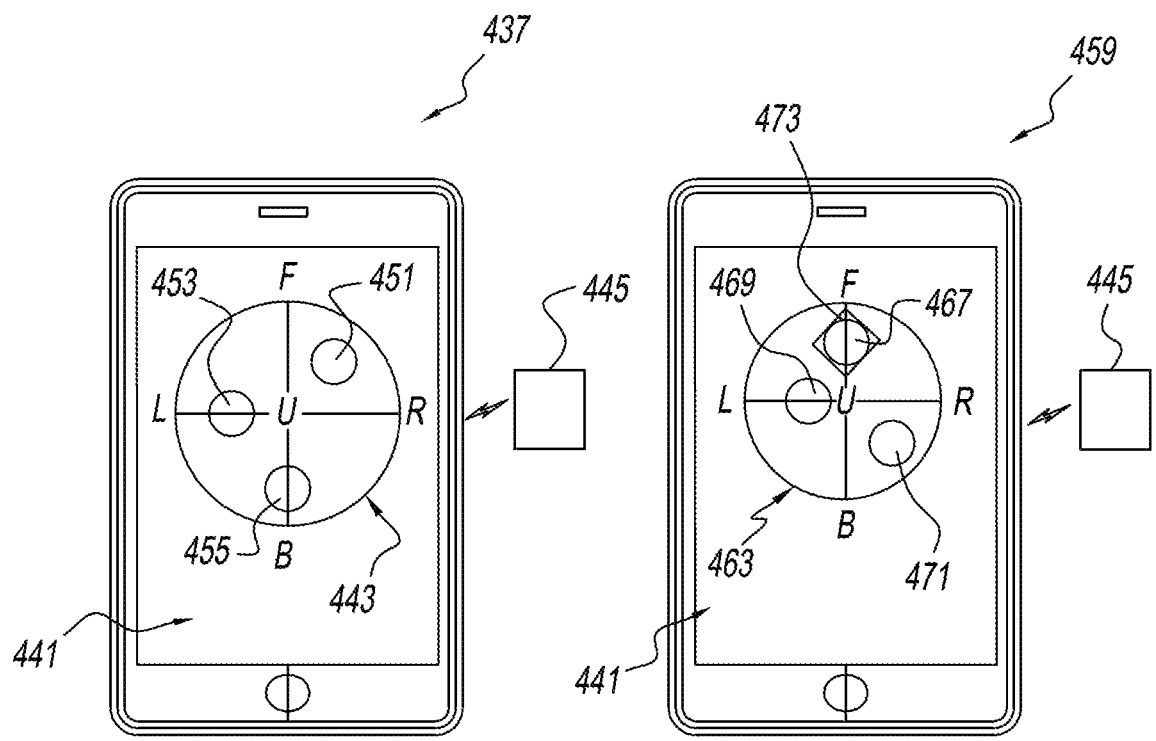
Figure 19C:
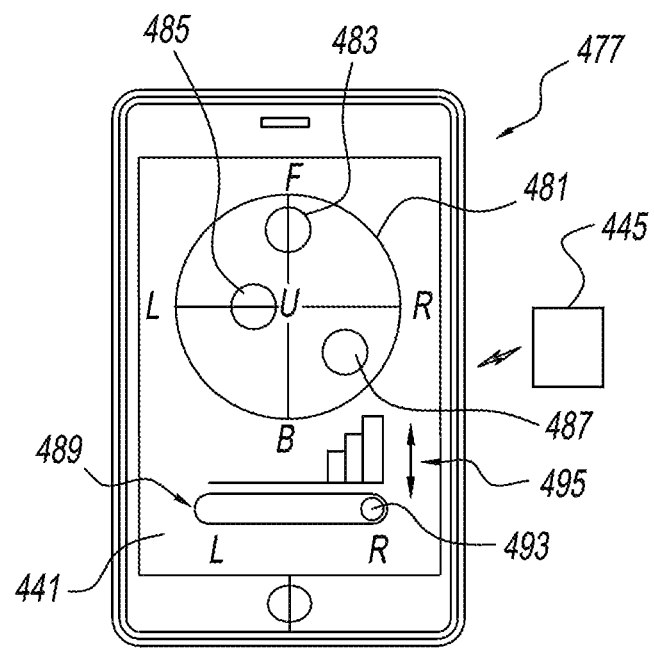
Figure 20:
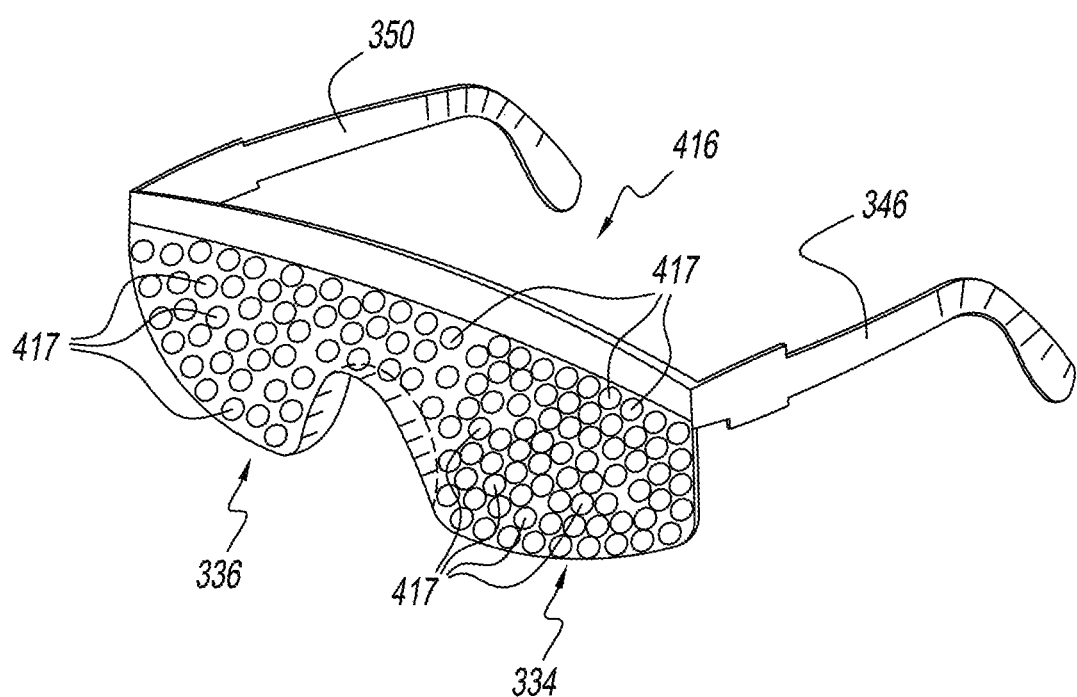
Figure 21:
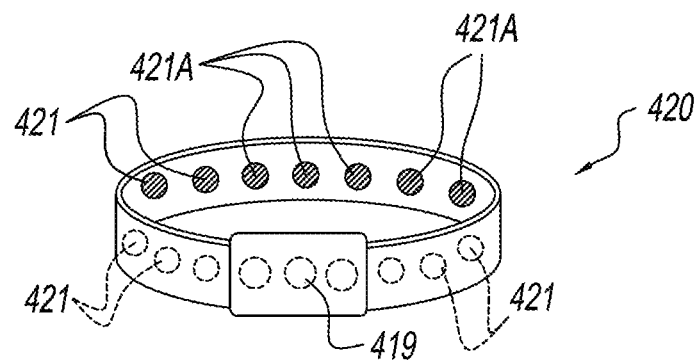
Figure 22:
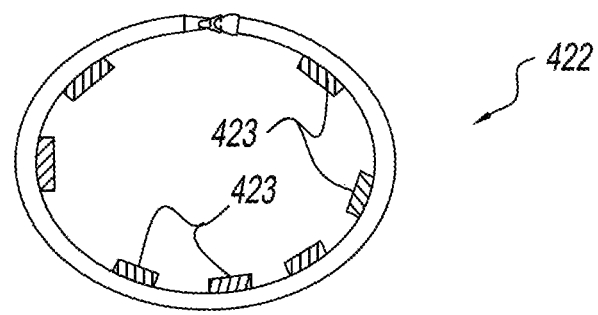
Figure 23:
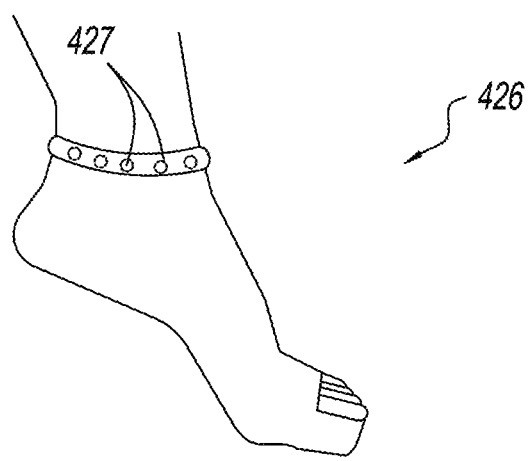
Figure 24:
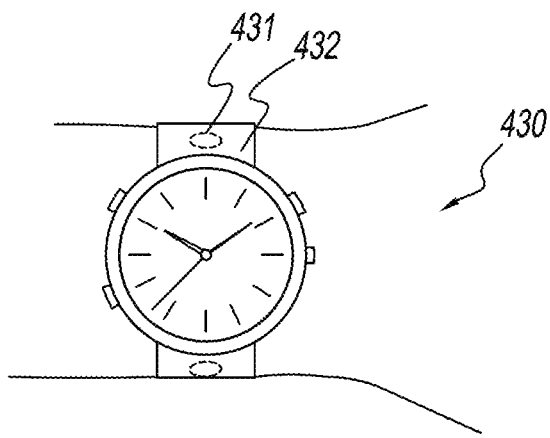
Figure 25:
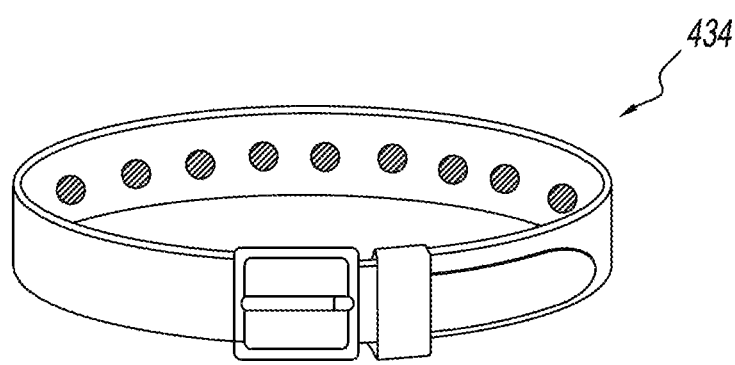

FIG. 10 is a frontal view of an exemplary hearing aid component that includes a tactile indicator member;

FIG. 11 is a schematic view of an asymmetric hearing aid device of the present invention that includes both a hearing aid component and a tactile or light-based indicator member;

FIG. 12 is an alternate embodiment asymmetric hearing aid device that includes a tactile indicator member shown as a necklace type device;

FIG. 13 is a perspective schematic view of a pair of eyeglasses fitted with tactile indicator member;

FIG. 14 is an alternate embodiment pair of eyeglasses that are fitted with both tactile indicator members and light-based indicator members;

FIG. 15 is an alternate embodiment pair of eyeglasses for use with an asymmetric hearing aid of the present invention that includes both light-based and tactile-based indicator member;

FIG. 16 is another alternate embodiment of a pair of eyeglasses usable with the asymmetric hearing aid in the present invention that include light-based indicia member;

FIG. 17 is another alternate embodiment of a pair of eyeglasses usable as a part of the asymmetric hearing aid of the present invention that includes a pair of rows of lights that serve as a light-based indicator member;

FIG. 18 is another alternate embodiment of a pair of eyeglasses that are usable with an asymmetric hearing aid of the present invention that incorporates an alternate embodiment light-based indicator of the present invention;

FIG. 19 is another alternate embodiment of a pair of eyeglasses that use a projection or internally generated image type of light-based indicator, and are usable as a part of the asymmetric hearing aid of the present invention;

FIG. 19A s another alternate embodiment that uses a cell phone having a screen that can serve as a visual type indicator in addition to or in lieu of other non-audible indicia generators;

FIG. 19B is another alternate embodiment cell phone employing embodiment that includes a controller that communicates with the second hearing aid to enable the user to vary the output of the second hearing aid, such as by altering it, adding to it or emphasizing certain portions of the output;

FIG. 19C is another alternate embodiment cell phone employing embodiment that includes a controller similar to FIG. 19B, that communicates with the second hearing aid to enable the user to vary the output of the second hearing aid, and also to enable the user to toggle back and forth between left and right side originating sounds and also provide a graphic representation of the sound being emphasized either relating to volume of the sound or frequency of the sound FIG. 20 is another alternate embodiment of a pair of eyeglasses that use a plurality of light points on the lenses to serve as light-based indicator members;

FIG. 21 is an alternate embodiment of a tactile indicator member usable with the asymmetric hearing aid of the present invention wherein a plurality of tactile members is coupled to a body wearable member, here shown as a collar-type necklace;

FIG. 22 is an alternate embodiment tactile indicator type member usable with the asymmetric hearing aid device of the present invention wherein the tactile members are incorporated onto a bracelet type member which can be used with a second bracelet (not shown);

FIG. 23 is an alternate embodiment tactile indicator type member here shown as being mounted onto an anklet;

FIG. 24 is another alternate embodiment tactile indicator member wherein tactile indicators, such as vibrators, are incorporated into either the band or body of a watch member;

FIG. 25 is another alternate embodiment tactile indicator member that is usable with the asymmetric hearing aid of the present invention, and which includes a plurality of tactile indicator members, such as vibrators, that are incorporated onto a wearable member, here shown as a belt.

Figure 26:
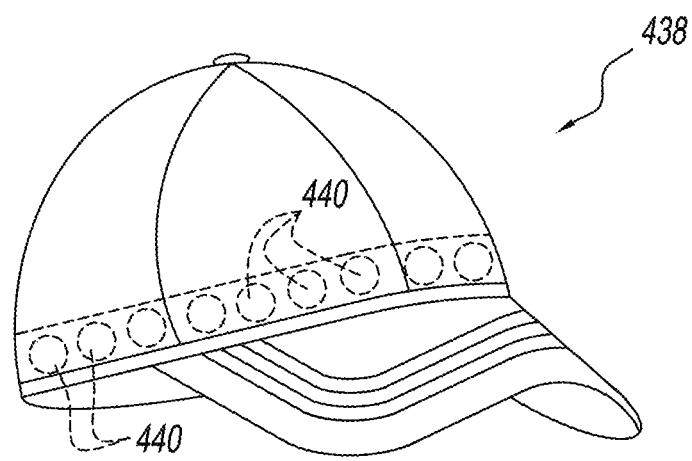

FIG. 26 is another alternate embodiment tactile indicator member that is usable with the asymmetric hearing aid of the present invention, and which includes a plurality of tactile indicator members, such as vibrators, that are incorporated onto a wearable member, here shown as a hat.

Figure 27:
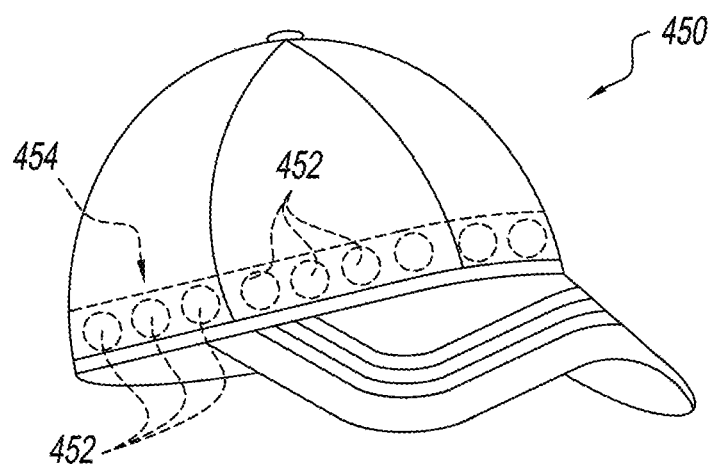

FIG. 27 is another alternate embodiment tactile indicator member that is usable with the asymmetric hearing aid of the present invention, and which includes a plurality of transducers such as microphones, and tactile indicator members, such as vibrators, that are incorporated onto a wearable member, here shown as a hat.

Figure 28:
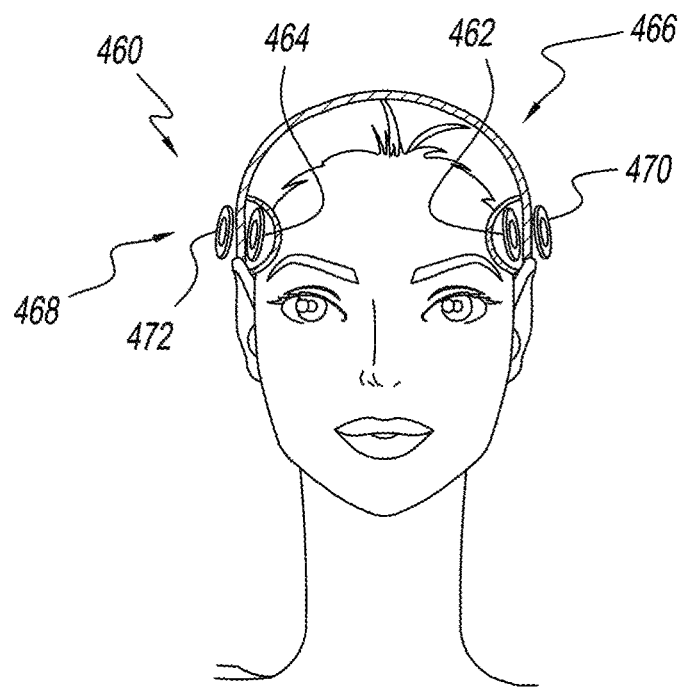

FIG. 28 is another alternate embodiment tactile indicator member that is usable with the asymmetric hearing aid of the present invention, and which includes a plurality of tactile indicator members, such as vibrators, or electrical signal generators that are implanted subcutaneously.

Figure 29:
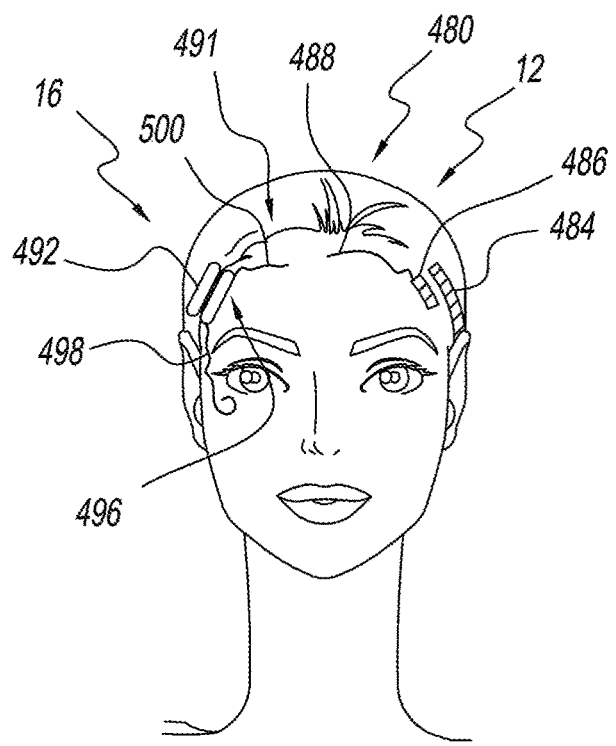

FIG. 29 is a schematic view of an alternate embodiment of an electrical stimulation indicator member that is subcutaneously implanted into a user.

Figure 30:
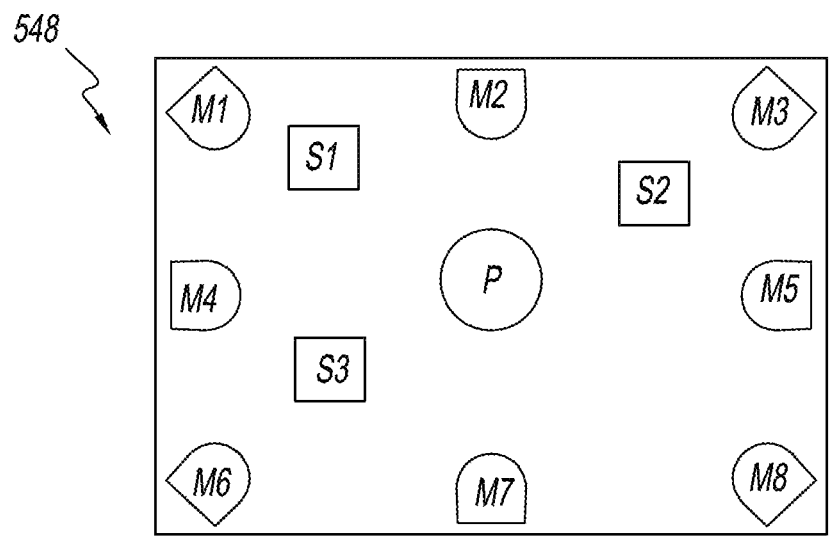

FIG. 30 is a schematic representation of a specially adapted space such as a conference room containing a plurality of microphones for helping to provide an indication of the origin of sound to a user.

Figure 31:
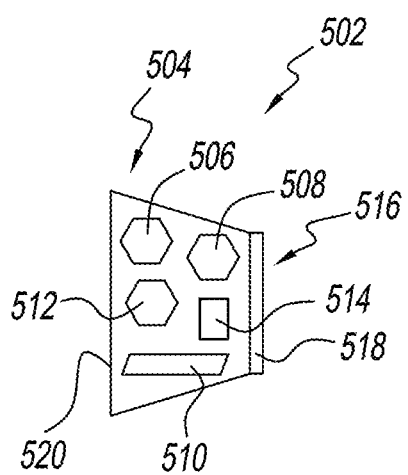

FIG. 31 is a schematic view of a universal type indicia generator that is capable of providing one or more of a tactile, electrical, and visual indicia.

Figure 32:
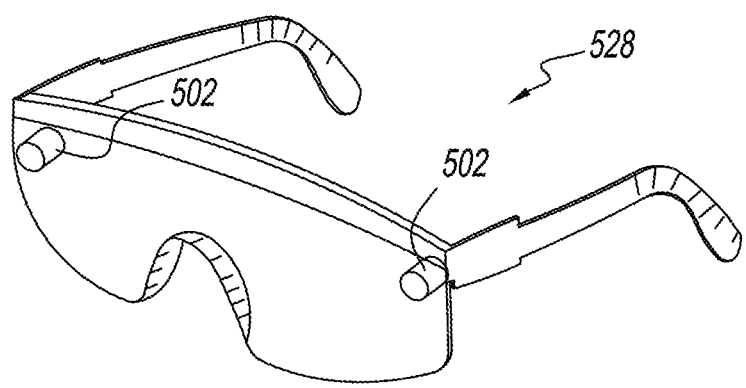

FIG. 32 is a perspective view of a pair of eyeglasses that incorporate the universal indicia generator of FIG. 31.

Figure 33:
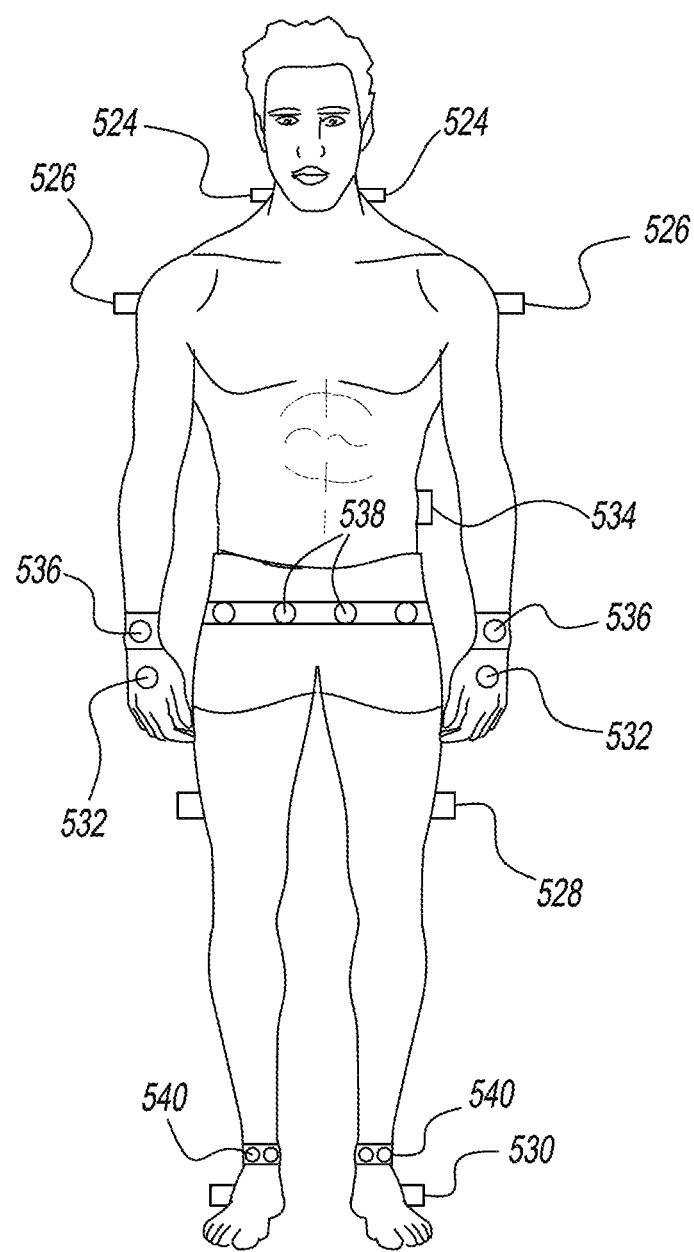

FIG. 33 is a schematic view of the universal indicia generator being employed at a plurality of potential locations on a user to provide stimulation at the points on which the indicia generator is positioned.

V. DETAILED DESCRIPTION OF INVENTION

The description that follows describes, illustrates and exemplifies one or more particular embodiments of the present invention in accordance with its principles. This description is not provided to limit the invention to the embodiment or embodiments described herein, but rather to explain and teach the principles of the invention in such a way to enable one of ordinary skill in the art to understand these principles and, with that understanding, be able to apply them to practice not only the embodiment or embodiments described herein, but also other embodiments that may come to mind in accordance with these principles. The scope of the present invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing reference numbers, such as, for example, in cases where such labeling facilitates a clearer description. Additionally, the drawings set forth herein are not necessarily drawn to scale, and in some instances, proportions may have been exaggerated to more clearly depict certain features. Such labeling and drawing practices do not necessarily implicate an underlying substantive purpose.

Furthermore, certain views are side views which depict only one side of the vehicle (or one set of components of a multi set array of components), but it will be understood that the opposite side and other component sets are preferably identical thereto. The present specification is intended to be taken as a whole and interpreted in accordance with the principles of the present invention as taught herein and understood by one of ordinary skill in the art.

There are also certain conventions with regard to language that are specific to this application. For example, the term "unilateral hearing loss" relates to a hearing loss wherein the hearing loss suffered by one ear is different from, and usually greater, than the hearing loss suffered by a second ear. As such, there may be hearing loss in both ears that fall within the term "unilateral hearing loss" as used in this application. However, as discussed above, the primary perceived use for the present invention at this time is for users who have a "unilateral hearing loss" wherein the difference in hearing loss between one ear and the other is significant enough to warrant the special consideration of using the hearing aid device of the present invention, rather than a more typical conventional hearing aid.

The term profoundly asymmetric hearing loss is used to identify a condition where the hearing loss of one ear is sufficiently great that sound amplification devices, such as hearing aids will not restore usable hearing acuity to that ear. Profoundly asymmetric also includes other conditions such as wherein the hearing of the bad ear cannot be restored without resorting to an invasively placed sound amplification device such as a cochlear implant.

A further convention used in this application, is that the terms "bad ear" and "good ear" are used. It will be appreciated that the term "bad ear" and "good ear" are relative terms, with the term "bad ear" being used to designate the particular one of the two ears that suffers a more profound hearing loss than the other ear.

To help maintain consistency in this application, the left ear 12 of the user P is usually designated as the "bad ear" and the user's right ear 16 is usually designated as the "good ear". Those skilled in the art will recognize that this choice of left and right as good and bad ears is purely arbitrary, and that it is just as likely that any particular user's right ear will be his bad ear, and that his left ear will be his good ear.

Figure 1:
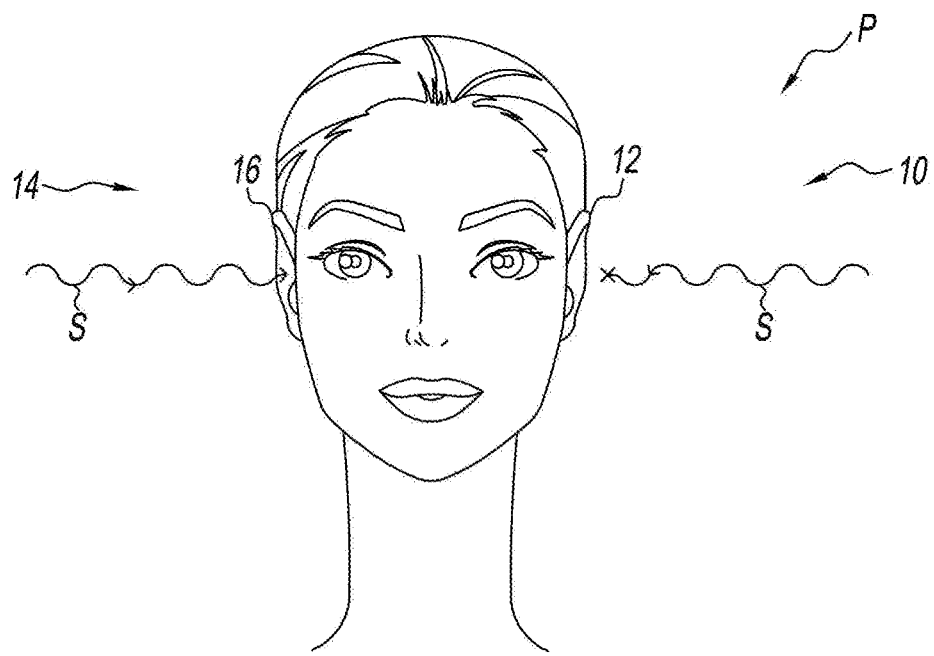
FIG. 1 is a schematic view of a user having a unilateral hearing loss, without correction, either via the prior art, or the instant invention.

Your attention is now directed to the figures that illustrate the invention and in particular, FIG. 1. FIG. 1 shows a user having a left side 10 that includes a left ear 12, and a right side 14 that includes a right ear 16. User P has a unilateral hearing loss. As illustrated in the drawings, the sound wave S that is shown adjacent to the left ear 12, includes an "X" at its distal end, to indicate that the sound wave reaches the ear, but does not penetrate into the hearing receptors within the brain of the user and as such the sounds are not "heard".

As discussed in the inventor's other ear related patent applications, all of which are incorporated by reference herein, the typical reason for such a hearing loss springs from malfunctions within one of the organs of the ear, such as the ear drum, the bones of the middle ear, or often the cochlea and its various component parts. A further discussion of diseases of the ear, and reasons for hearing loss are available from a wide variety of sources, and particularly textbooks relating to diseases of the ear.

By contrast, the sound wave arrow S that is shown adjacent to the right or good ear 16 has an arrow at the end. The use of the arrow is a convention adopted in this application to indicate that the right ear has some auditory acuity, or in particular, greater auditory acuity and hearing capability than that of the bad or left ear 12. As will be discussed in more detail below, users exist who have a profound or total hearing loss in their bad ear 12, but perfect hearing in their good ear 16. Other users exist who have a hearing loss in both their good ear 12 and their bad ear 16, although the hearing loss in their bad ear 12 is more profound than the hearing loss out of their good ear, thereby resulting in a profound asymmetric hearing loss.

Figure 2:
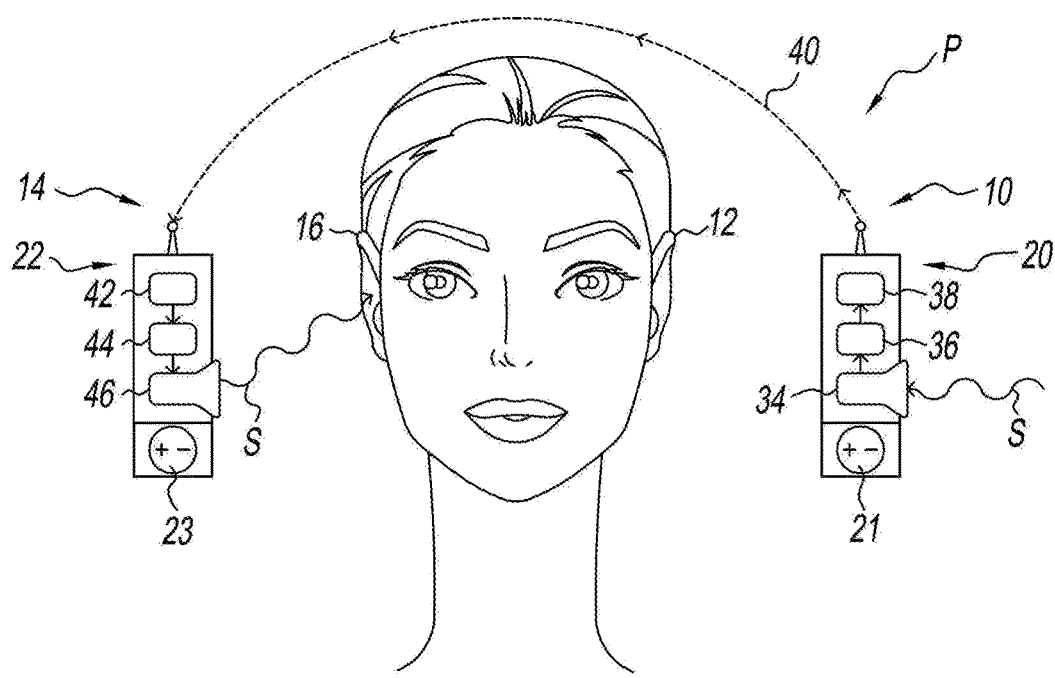
FIG. 2 is a schematic view of a user having prior art CROS hearing aid system used for treating a unilateral hearing loss.

A prior art device used for treating unilateral hearing loss is shown in FIG. 2.

In FIG. 2, a user is shown having a left side 10 and a right side 14, a left ear 12 and a right ear 16. User P also has a hearing aid apparatus that is shown schematically as comprising a first hearing aid member 20 that is designed for placement on the bad ear side 10 of the user and preferably placed adjacent to or in the left or bad ear 12. The hearing aid apparatus also includes a second hearing aid member 22 that is placed on the good hearing side 14 adjacent to the good ear 16 and is provided for broadcasting sound waves S into the user's ear so that the user can have a hearing sensation.

To help understand the operation of the present invention, the hearing aids 20, 22 shown in FIG. 2, along with the hearing aids shown in the remainder of the application are shown schematically, and are positioned in a spaced relation from the user's head, so as to help keep the drawings more clean. However, in practice, a hearing aid will be employed that likely has an appearance and external construction similar to the prior art hearing aid shown in FIG. 7. As shown in FIG. 7, the prior hearing aid 26 includes an ear globe portion 28, a case portion 30, and a connector 32 for connecting the case 30, with the ear globe 28. The case 30 includes an interior space for housing the circuitry for the device 26, along with batteries to power the device 26. Additionally, the case 30 may include various circuitry for processing sound along with a microphone-type transducer for picking up ambient sound around the user's ear.

The hearing globe 28 is preferably designed to be custom molded to fit snugly and securely within the user's ear. The hearing globe 28 can include processing circuitry and a first transducer such as a microphone, if it is preferred to place one in the globe 28 rather than the casing. However, the primary component that is contained within globe 28 is a second transducer, such as a loud speaker type transducer that is provided for broadcasting or delivering sound into the user's ear and more particularly, into the ear canal of the user's ear, so that the sound delivered therein can impact the user's eardrum, which in turn, activates the bones of the middle ear, which in turn actuate the cochlea, and the various components therein.

In addition to the hearing aid shown in FIG. 7, the reader's attention is directed to discussions of other hearing aid cases and types that likely would also serve as suitable casings for the present invention. For example, larger, cigarette pack-sized body cases are used with some hearing aids, since they have greater room for additional circuits and have greater room to hold batteries to provide them with a longer battery life. The body cases also usually have less expensive manufacturing costs and circuitry costs due to the fact that the greater volume of the case provides room for additional batteries, and reduces the enhanced costs associated with ultra-miniaturization of components, as must occur to get all the appropriate components and batteries to fit within a small size case such as the behind-the-ear case 30 shown in FIG. 7.

A schematic representation of the prior art hearing aid 10 is shown in FIG. 2, as including a first hearing aid member 20 that is placed adjacent to the user's bad ear 12, and a second hearing aid member 22 that is placed adjacent to the user's good ear 16. The first hearing aid 20 includes a power source such as a battery 21 to provide power for the electrical circuitry within the hearing aid. A battery 23 is also provided in second hearing aid 22 to provide power to the electrical circuitry within the hearing aid 22.

Battery members that will work well are known within the prior art. Although battery members 21, 23 are shown in the prior art hearing aids, 20, 22, they are not shown in the remaining hearing aids of the present invention. However, it will be understood that the absence of showing the power sources within these hearing aids of the present invention is not an indication of a lack of a power source in the devices. Rather, the power sources were not shown to simplify the drawings, as it will be well understood that conventional power source batteries would likely usually need to be included in each of the hearing aid members of the present invention.

The transducer 34 is a microphone type transducer that is assigned to pick up ambient sounds that would otherwise be picked up by the user's ear. Sound waves S that enter the transducer, are "transduced" from sound wave signals to electrical signals that are delivered to a processor 36. Processor 36 performs some processing on the signal before delivering the signal to transmitter 38. Transmitter 38 is provided for sending a wireless signal 40 to a receiver 42 that is housed within the second hearing aid member 22.

For purposes of illustration, the transducer 34, processor 36 and transmitter 38 are shown as separate components. However, it will be appreciated, that the components can be designed to be a single unit or designed in any other manner that provides a product that serves its intended purpose and meets all performance, size and cost-requirements.

The external antenna shown on the hearing aid 20 is shown also for illustrative purposes, it being envisioned that an internal antenna will be used in the actual model.

The hearing aid member, that is placed adjacent to the good ear 16, is preferably designed to have an appearance similar to the hearing aid shown in FIG. 7. The hearing aid includes a receiver 42 for receiving the wireless signal from transmitter 38 of the first hearing aid member 20. It has been found that a wireless transmitter is much preferred over a wired transmitter for reasons of convenience and aesthetics. The electrical signal received by receiver 42 is transmitted to a processor, which may perform little to no processing, or may just be a processor such as an amplifier that amplifies the signal prior to sending the signal to the transducer 46. The second transducer 47 comprises a transducer such as a loud speaker, for converting electrical energy to sound energy S. The sound waves S are broadcast into the ear canal of the user, for delivery to the ear structure including the ear drum that is disposed at the inner portion of the ear canal.

Figure 3:
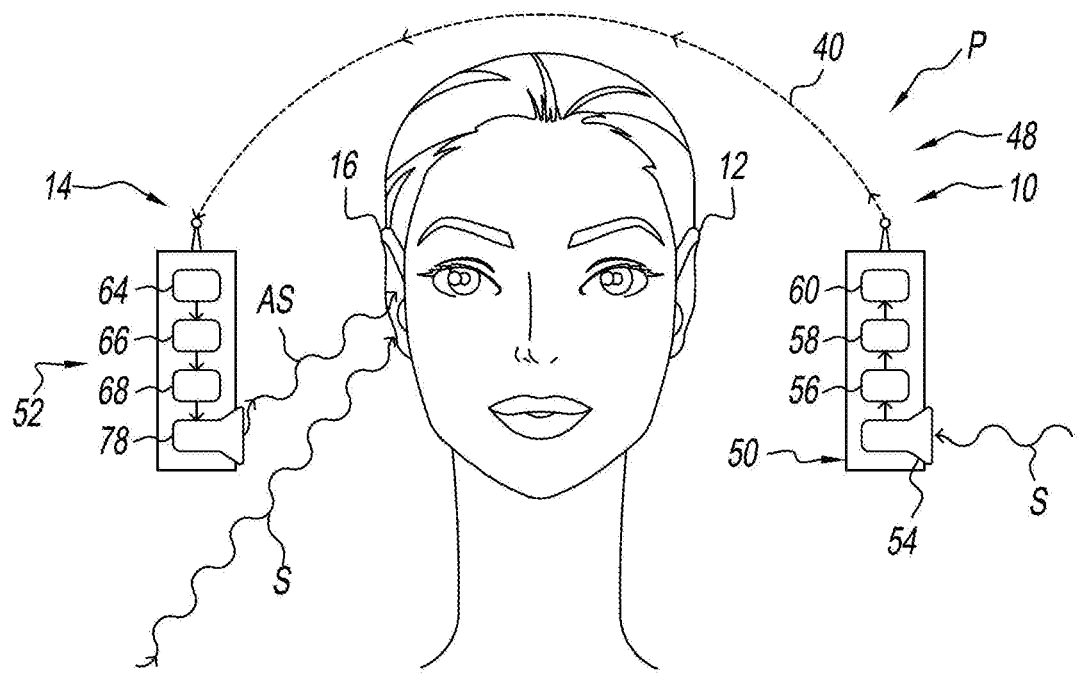
FIG. 3 is a schematic view of a user having a CROS type hearing aid system of the present invention to help treat a unilateral hearing loss.

A CROS-type hearing aid system 48 of the present invention is shown in FIG. 3. A CROS system is normally employed when the bad ear has a significant or profound hearing loss, but the good ear has hearing within the normal range, and as such, does not need the amplification that is provided by a typical hearing aid.

The hearing aid system 48 of the present invention includes a first hearing aid member 50 that is placeable on a user's body and is usually positioned on the same side 10 of the user's body as the bad ear 12 for receiving sounds that would normally be received by the user's first ear 12. A second hearing aid member 52 is also provided that is placeable on a user's body adjacent to the user's second or good ear 16. As a second hearing aid member is provided for broadcasting sound information into the user's good ear 16, it is preferred that the second hearing aid member 52 be positioned on the user's ear, so that the sound produced by the transducer 78 of the second hearing aid member can be delivered directly and closely to the user's ear structure, such as the user's ear canal and eardrum.

The first hearing aid member 50 includes a first transducer 54 that is provided for receiving sound energy S. Sound energy S is preferably of the type and nature of sound energy that would normally be picked up by the user's bad ear 12 if the user's bad ear 12 had normal hearing. The transducer 54 is preferably a microphone transducer.

As will be appreciated by those familiar with the microphone art, various types of microphone transducers are available but have different "pick-up patterns". The pick-up pattern for a particular microphone is chosen depending upon the nature of the sound that is desired to be picked up. For example, some microphone transducers in use in applications other than hearing aids comprise conference-type microphones that are designed to pick up sound signals in an omnidirectional pick-up pattern including those sound signals that are delivered close to the microphone, and also those sound signals that are relatively far away from the microphone. On the other hand, other microphones may be unidirectional and designed to only pick up sounds that are delivered very close to the microphone, so as to reduce the background noise picked up by such microphones. The choice of preferred transducer is determined by the user and medical practitioner and is chosen to best serve the purposes that are intended for the microphone transducer 54.

The transducer 54 is provided for converting sound energy into a first electrical transmittable signal that is transmitted to a first signal processor 56. The first signal processor 56 processes the signal such as by amplifying it, conditioning it, or the like.

The first processor 56 then forwards a transmitted signal to a signal alteration processor 58. The purpose of signal alternation processor 58 is to alter the signal so that there is an altered sound AS that is produced different than the sound signal S that is delivered in the user's ear.

Although the drawings show the processors 56, 58 as being separate units, it is important to note that this is done for purposes of illustration and clarity. In practice, it is likely that a single processor will be used that will engage in traditional functions such as amplification of the signal, along with alteration functions.

The altered signal that emerges from altered signal processor 58 is then transmitted to a transmitter 60 that transmits a wireless signal to a receiver 64 of the second hearing aid member 52. Receiver 64 is generally similar to the receiver of the prior art hearing aid. The signal received by the receiver 64 is forwarded to a signal processor 66 that then forwards the signal to a signal alteration processor 68.

Depending upon the signal, and the functionality of the device, it is likely that there is a need for only one signal alteration processor. As such, in practice, either signal alteration processor 58 or signal alternation processor 60 can be eliminated. The purpose of showing a pair of signal alternation processors 58, 60 is to illustrate that the signal alteration processing function can be contained here within the first hearing aid member 50 or the second hearing air member 52, at the choice of the designer of the unit. Additionally, it is possible that the electrical sound signal that passes through the first and second hearing aid members 50, 52 requires only processing by a single processor, thus permitting the user and/or designer to eliminate one or both of conventional signal processors 56, 66.

The output of the second hearing aid member 52 comprises an altered signal AS that is delivered to the user's ear. Additionally, since the user does not have a hearing loss in her good ear 16, the user would also receive ambient sound S into her ear. Therefore, two streams of sound information, including sound S and altered sound AS are being fed into a single ear 16. The user is obtaining two channels of information in a single ear 16, which results in monoraul hearing rather than the stereophonic or binaural hearing that is enjoyed by a person with hearing acuity in both ears.

The alteration incorporated into the altered signal is intended to help remedy this problem by creating an altered signal that has a sound that is distinguishable from the primary signal S, so that the user, after a learning interval, can distinguish between an altered signal AS and a regular signal S. By so recognizing the altered signal AS, the user can learn to appreciate directionality, as the user should learn to recognize the altered signal AS and recognize that the altered signal comes from the user's bad ear 12 side 10 rather than from the user's good ear 16 side 14.

Figure 4:
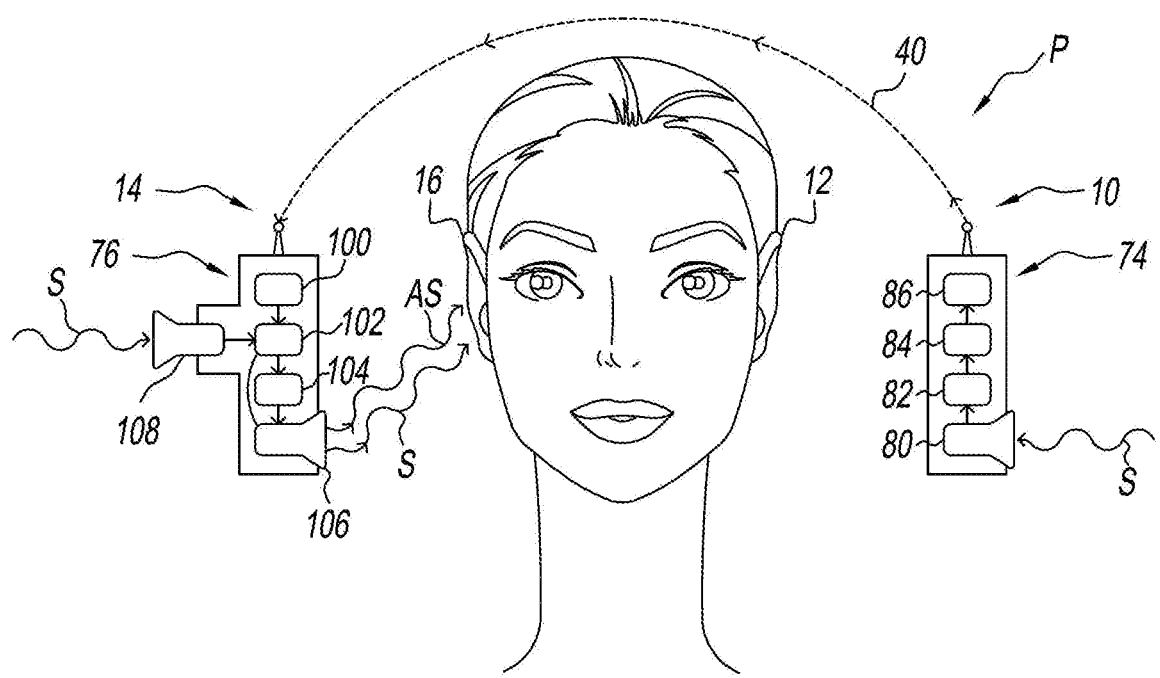
FIG. 4 is a schematic view of a user using a BICROS hearing aid system of the present invention to help treat a unilateral hearing loss.

Although the signal from the user's bad ear side 12 is shown as being the altered signal, it will be appreciated that the roles could be reversed, such as in the BICROS device of FIG. 4, which processes both the regular signal S and the altered signal AS, such that the altered signal emanates from the user's good side 14 and the regular unaltered signal emanates from the user's bad ear 12 side 10.

The purpose of using a signal alteration processor is to alter the sound from either the user's bad ear side, or the user's good ear side, so that the altered one of the first and second sound signals and the other non-altered of the first and second sound signals will have distinguishably different sound characteristics, when converted to electrical signals to sound signals. A variety of vehicles exist through which the sound can be altered. For example, the sound can be altered by changing its pitch, so that the altered sound has a higher or lower pitch than the non-altered sound. Additionally, an echo can be induced into the altered sound so that it sounds different. Further, one can delay the signal, so that the first and second signals are off set temporally. Delaying the sound temporally helps to provide a difference that may be distinguishable.

Further, the signal can be filtered such as by passing it through a high pass or a low pass filter, to change the characteristic of the signal. Through this, the pitch of the signal for example can be lowered or raised. Further, a chorus effect can be added to the signal, such that one signal plays at a harmonic to a second signal, or at least sounds as though it is a second signal distinct from the first sound signal.

Also, different frequency bands can be attenuated to alter the signal. Another way of altering the signal is to resonate the signal. Further, an artifact can be added to the signal. An artifact such as a hum or a click or a tone or the like can be added to one signal so that the user can distinguish the artifact added signal from the "clean signal". Further, the strength of the signal can be changed to alternate the volume. Another way of treating the signal to alter it is to modulate the signal.

There are several ways that artifacts can be added. These artifacts can include a vibration added to the sound, a humming sound, or an added tone to the altered signal. A sound artifact or sound transformation is preferably incorporated into the altered signal so that the sound has a difference from the sound as being received from the user's other ear. As discussed above, either the bad ear signal or the good ear signal can be altered, depending upon user preference. Preferably, the signal alteration processor 58 or 68 adds some type of sound artifact or sound transformation so that the user can tell the difference between the first altered signal, and the second unaltered signal from the other ear.

In one embodiment, the artifact that is inserted is a distinct sound difference that is added onto the signal. For example, the tone can be a multi-type tone, a crackling type tone, a clicking type tone, a hum type or other type of tone. Any number of additional added sounds could be used to distinguish the first altered sound signal from the second, unaltered sound signal so that the user can differentiate between a sound picked up by the user's "good ear" and a sound picked up by the user's "bad ear".

By adding an artifact to the signal of one hearing member such as the first hearing member 50 that picks up sound adjacent to the user's bad ear 12 but not the signal received into the user's good ear, such as sound signal S of FIG. 3, or the sound signal picked up by transducer 108 in the BICROS embodiment of FIG. 4, the user effectively hears two signals of information, one with an artifact and one without an artifact. Over time, the user will be able to differentiate between the two signals to help the user distinguish between the artifact containing signal and the non-artifact containing signal.

Ultimately, the user will come to recognize that the artifact containing signals emanated from his bad ear side (in a case where the bad ear side signal is altered), and the non-artifact signal was emanating from the user's good ear 16 side 14. Through this process, the user will be able to gain some sort of simulated stereophonic hearing in geolocation of sound.

Another artifact that can be incorporated is a voice transposition type of artifact. In a voice transposition type of artifact, one might alter the tone of the signal coming from the first hearing aid member 50, as compared to the tone coming from the good ear side 14. For example, the tone could be raised an octave or lowered an octave. Additionally, the sound could be altered to sound more "tinny" to sound "deeper" or the like.

Preferably, the hearing aid device 48 is designed so that it can be programmed by the user to provide different artifacts of the user's choosing. For example, some might wish to have an altered sound coming from the bad side (hearing member) to include an artifact that changes the sound to simulate that of a famous actor, voice talent or the like, or a cartoon character. In operation, the user would be given a first hearing aid member 50 and a second hearing aid member 52 into which a suitable artifact would be programmed.

FIG. 4 shows a hearing aid system 72 that comprises a BICROS type system. As discussed above, a BICROS system is used when the user has a hearing loss in both his bad ear 12 and his good ear 16, so that both the signals from the bad side 10 and good side 14 need to be treated by hearing aids.

A BICROS system includes a first hearing aid member 74 and a second hearing aid member 76. First hearing aid member 74 is generally similar to first hearing aid member 50 shown in three of the CROS design. In particular, first hearing aid member 74 includes a transducer 80 that comprises a microphone, for receiving sounds S. Preferably, the first hearing aid member 74 is positioned close to the bad ear 12 of the user, so that the sounds S picked up by the first transducer can positionally replicate the sounds that would be picked up by the user's bad ear 12, if the ear were working properly.

The first transducer 80 is provided for converting sound energy to a transmittable electrical signal that is transported to the first signal processor 82. The first signal processor 82 processes the signal and forwards it to a first signal alteration processor 84, that is provided for adding the artifact or otherwise altering the sound so that the altered sound AS that is delivered by the second transducer 106 of the second hearing aid member 76 is sufficiently distinguishable from the unaltered sound S, so that the user can hear the difference and distinguish the difference between the unaltered sound S and the altered sound AS that is delivered to the ear.

The electrical signal that emanates from the signal alteration processor 84 is then delivered to transmitter 86 which transmits a wireless signal 40 to the receiver 100 of the second hearing aid member 76. The receiver 100 delivers a signal to a signal processor 102, and a signal alteration processor 104. The altered signal is then forwarded to the second transducer 106, which broadcasts both an altered sound signal AS and an unaltered sound signal S into the user's good ear 16.

In this regard, the second hearing aid member 76 is similar to second hearing aid member 52 of the CROS member. However, a difference with the second hearing aid member 76 is that the second hearing aid member 76 also includes a first transducer 108 that preferably comprises a microphone type transducer, similar to first transducer 80 of the first hearing aid member 74. The first transducer 108 is provided for picking up sound signals that are similar due to its 108 position, to the sound signals that would be picked up by the user's good ear 16, if the user's good ear 16 did not need augmentation.

The sound picked up by the first transducer 108 can also be delivered through the signal processor 102 that processes the signal separately from the altered signal, and delivers the signal that emanates from the processor 102 to the transducer 106. Preferably, the signal that comes from the first transducer 108 bypasses the signal alteration processor 104, so that no alteration is made of the signal that originates from the first transducer 108.

Nonetheless, it may be worthwhile to perform some processing on the signals through the signal processor 102, such as by amplifying the signal, or changing the volume of the signal so that the sound signal delivered by the second transducer 106 to the ear of the user will be at an appropriate volume.

Figure 5:
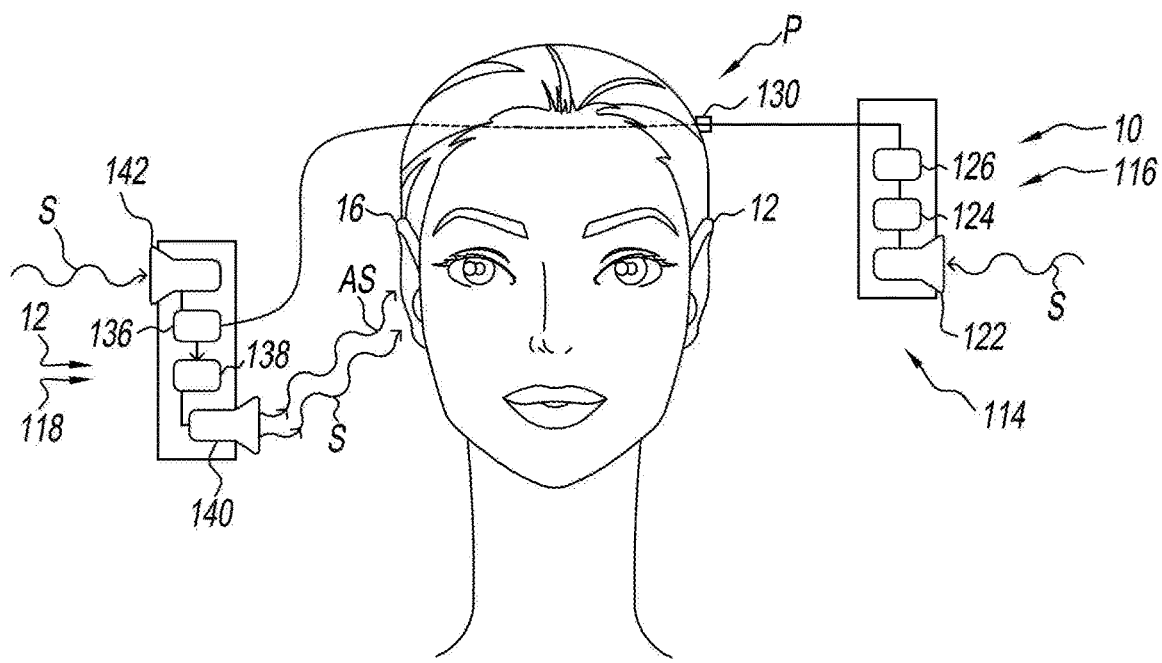
FIG. 5 is a schematic view of a user having a BAHA type hearing aid system of the present invention for treating a unilateral hearing loss.

A BAHA (bone anchored hearing aid) system 114 is shown in FIG. 5. As discussed above, a primary difference between a BAHA type system 114, and the other system such as discussed herein is that a BAHA system transmits signals from the first hearing aid member 116 on the bad ear side 12 to the second hearing aid member 118 on the good ear side 14 by using the skull bone of the user as a medium through which to transmit sounds and vibrations.

As sounds are being transmitted through the bone, the signal processor used within the hearing aid tends to be amplifier-type processors. A wireless transmitter and receiver are not needed as no wireless signal is being transmitted between the first hearing aid member 116 and the second hearing aid member 118.

The BAHA hearing aid system 114 includes a first hearing aid member 116 that is positioned on the user somewhere near the bad ear 12 side of the user to receive sounds. A second hearing aid member 118 is placeable on the good ear 16 side of the user and is provided for delivering sound waves S into the ear 16 of the user. As has been used conventionally herein, the "AS" wave is for the altered sound wave, whereas "S" is for an unaltered sound wave.

The first hearing aid member 116 includes a first transducer 122 of a microphone-type for receiving ambient sounds that would normally be picked up by the user P's ear, if the user's bad ear 12 were normal. The first transducer feeds the signal to a first signal processor 24 which feeds the signal to a first signal alteration processor 126.

The alteration signal processor 126 inserts an alteration to the signal, such as a change in tone, or the addition of an artifact, so that the signal becomes distinguishably different from an unaltered signal to help the user P distinguish between the signal received from his left side through the first hearing aid member 116 in the signal received by the user's right side by the second hearing aid member 118. As also discussed above, the present invention contemplates that a signal will be altered. However, it is not limited to altering the signal in the first hearing aid 116, as the signal can just as well be altered by the signal alteration processor 138 of the second hearing air member. The second hearing aid member 118 includes a first signal processor 126 for processing the signal received from the first hearing aid member 116.

A bone screw 130 couples the first hearing aid member 116 to the skull of a user, so that vibrations induced in the bone screw 130 can be induced into the skull, and transmitted through the user's skull to a suitable receiver or wire that transmits the bone signal to the first signal processor 136 of the second hearing aid member 118. The signal from this first signal processor 136 is conveyed to the signal alteration processor 138 which may or may not exist, depending upon whether the signal alteration is handled by the signal alteration processor 126 of the first hearing aid. The altered signal AS is then transmitted to the transducer 140 of a loud speaker type that then converts the electrical signal energy into audio energy.

The BAHA hearing aid system 114 of the present invention is shown as being a BICROS system that includes the first transducer 142 of a microphone type that is part of the second hearing aid member 118. The transducer 142 picks up ambient sound waves S and then converts it into an electrical signal, and then delivered to the first signal processor 136, and ultimately to the transducer 140, where the sound is reconverted into a sound type signal S.

Although the convention discussed herein has normally contemplated that the sound picked up by the first hearing aid member 116 will be altered to produce the altered signal AS, it is also contemplated that the sound picked up by the first hearing aid member 116 could be unaltered with the sound S being picked up by the first transducer 142 of the second hearing aid member 118 from the user's good ear 16 side being processed through the signal alteration processor 138 to produce the altered signal. As such, it is not necessarily that important which of the two signals (good side or bad side) is altered, so long as one of the two signals is altered so that the two signals sound different.

Conceivably if it would help the user to distinguish the two sounds coming from different sides of his head, it is possible that both of the sound received from the bad ear side 12, and the sound received from the good ear 16 side could both be altered.

Another embodiment is shown in FIG. 6 that includes an indicia indicator to also help the user better determine directionality. The two particular types of indicia shown in FIG. 6 include a light indicia and a vibrational indicia. Although both a light and vibrational indicia can be used with the same user, it is contemplated that normally one of the two will be selected, as the use of two indicia may be something of an over kill.

The indicia containing hearing aid system 146 includes a first hearing aid member 150 that is disposed on a user's bad ear 12 side, and a second hearing aid member 152 that is disposed on the user's good ear 16 side. A user P shown as wearing a pair of eyeglasses 154, upon which a first light-based indicia 156 is mounted, and a second light-based indicia 158 is mounted. To aid in directionality, the first light based indicia 156 is mounted closer to the user's left eye and is designed to turn on and emit light in some fashion that correlates with sound that is being picked up by the first transducer 166 of the first hearing aid member 150 that picks up the sound from the user's bad ear 12 side.

The second light indicia member 158 is positioned adjacent to the user's right eye and is designed to give off light that correlates to sound S that is being picked up by the first transducer 188 of the second hearing aid member 152 that is positioned on the user's good ear 16 side.

The light indicia 156, 158 are designed to help the user determine directionality because the user will be able to associate the light emitted by the respective first and second lights 156, 158 with the sound that he is hearing S, AS that is generated by the transducer 186 of the second aid member 152. This use of both sound and tactile and light differentiating indicia is believed to be useful in helping the user distinguish the sounds and hence, be able to get a simulated directionality from the sounds.

The vibration (second) indicia member comprises a first vibratory indicia member 158 that is positioned on the user's bad ear 12 side and a second vibratory indicia member 160 that is positioned on the user's good ear 16 side. The vibration induced in the user by the first and second vibrational members 158, 160 should correlate with the sounds being received on the user's bad ear 12 side and the user's good ear 16 side respectively. Although the vibratory members 158, 160 are being shown as being placed on the user's neck, the vibration members can be placed anywhere that is convenient and distinguishable by the user, including into the hearing devices (e.g., hearing aid, cochlear implant, BAHA device, etc.).

The vibratory members 158, 160 and light indicia members 154, 158 may all include wireless receivers for receiving a wireless signal from the respective first and second hearing aid members 150, 152 and be able to respond to those wireless signals to turn on and off respectively.

The indicia containing hearing aid system 146 includes a first hearing aid member 150 that includes a first transducer for receiving sounds that can be picked up from the user's bad ear 12 side. The transducer 166 is a microphone transducer that converts sound energy into a transmittable electric signal that is conveyed to a first signal processor 168 that then conveys the signal to a signal alteration processor 170. As discussed above, the signal alteration processor 170 can alter the signal such as by changing its tone, volume, pitch or adding an artifact, so that the sound has an auditorily distinguishable sound from an unaltered signal.

The sound is then conveyed to a wireless transmitter 174 that sends a wireless signal 177 to a wireless receiver 180 of the second hearing aid member 152. Second hearing aid member 152 includes a wireless receiver, which receives the signal 177 from the first hearing aid member 150, and conveys the signal to a signal processor 182, and then, optionally, to an alteration signal processor 184. The signal that leaves the alteration signal processor 184 is then delivered to a second transducer 186 of a loud speaker type that converts the electrical signal into a sound energy signal. As the signal has been altered, the sound signal which is produced by the second transducer 186 is the altered signal AS that is delivered to the user's ear.

It will be noted that the circuitry is schematically represented in second hearing aid member 152 in a slightly different manner from the manner in which the circuitry is illustrated in the other embodiments. In particular, the circuitry of the second hearing aid member 152 shown as having two distinct and non-overlapping circuit paths, wherein the signal 177 that is received from the first hearing aid member 150 follows a completely different path and is processed by a completely different components than the signal received by transducer 188 of the second hearing aid member. It will be appreciated that benefits and drawbacks exist with such a separate circuitry design, as opposed to the combined circuitry shown on the other embodiments.

The second hearing air member 152 includes a first transducer 188 that picks up ambient sounds on the user's good ear 16 side and converts those sounds into an electrical signal that is then directed to a signal processor 190. The signal processor 190 sends out two streams of information, including a first stream of information that is sent to a signal alteration processor 182 that then conveys the sound to the second transducer 186, where it is converted from an electrical signal into a sound signal S. The second stream of information is fed to an indicia signal processor 194 that includes a wireless transmitter for transmitting an indicia signal to one or both of the light indicia 158, and vibratory indicia 160.

In use, the hearing aid system 146 of the present invention receives sound information from each of the bad ear side 12 and good ear side 16. In addition to the sounds being processed so that you have an altered sound signal AS that is distinguishable from an unaltered sound signal to enable the user to help distinguish between the sounds received on his bad ear 12 side and his good ear side, an indicia such as the light indicia or vibratory indicia are also provided to correlate with the sounds to provide the user with another source of information relating to the direction from which the particular sound emanates, to better help the user achieve a sense of directionality from the sound, even without the stereophonic hearing that is provided to normal hearing persons through the use of two functioning ears.

In an alternate embodiment hearing aid of the present invention that employs a cochlear implant type device as one of its members is shown in FIGS. 8, 8A, 8B, and 8C.

The asymmetric hearing aid system 200 shown in these figures is provided for use with a user having a first ear 12 and a second ear 16. The hearing aid apparatus 200 is configured for enabling the user to hear sounds that originate from a plurality of directions. The hearing aid apparatus 200 includes a first hearing aid member 203 that is placeable on the same side of the user's body as the first ear 12. The first hearing aid member 203 includes a first transducer 204 for receiving sounds that would normally be received by the user's first ear 12 and converting those received sounds into first transmittable electrical signals 205.

One use of the hearing aid 200 of the present invention is with users who have extreme hearing loss issues. Typically, an asymmetric hearing aid most often serves the greatest potential good to a user who has a hearing loss that is sufficiently profound so that a normal approximately symmetric hearing condition is incapable of being substantially restored with an amplification adjusted hearing aid, thus requiring the asymmetric hearing aid of the present invention.

In its preferred embodiment the hearing aid 200 employs a pair of signals that simulate the sounds that would be received from both the first body side and second side, and feeds these signals into a single ear in a manner that enables the user to differentiate between the first sound signal that emanates from the first body side, and the second signal that emanates from the user's second body side. As will be discussed in more detail below, this signal differentiation can be accomplished through a variety means including different audio tones, artifacts being placed into one of the signals, or the use of other indicator to accompany the audio signal such as a tactile indicia caused by vibration or a light indicia which accompanies of the signals.

The second hearing member 208 is placeable on the user's second body side, and preferably comprises a cochlear implant device 201. The cochlear implant containing second hearing aid member 208 includes cochlear implant-type member 250 that is placeable within the user's cochlear that terminates at an electrode array 252, that is provided for providing electrical signals to the cochlear receptor nerves to simulate hearing in the user. The electrode array 252 is positionable within the interior of the cochlea of the user.

The cochlear implant containing second hearing aid 208 includes a second transducer/microphone 232 for receiving sounds that would be received by the user's second ear 16 and converting the received sounds into second electrical signals. The cochlear implant containing second hearing aid 208 converts the received sounds into second electrical signals.

Additionally, the housing member 218 of the externally disposed component 212 can also include second and third functional members 235, 237. The first members 235, 237 can comprise second and third microphone/transducers that have pick up patterns that are different to provide better directionality. For example, transducer 232 can be designed to pick up sound primarily from the side of the user, transducer 235 from the front of the user, and 237 from behind the user.

Alternately, elements 235, 237 can be tactile indicia generators that vibrate in response to sound being picked up by transducer 232.

A receiver processor 234 is provided for receiving the first transmitted electrical signals 205 and includes a processing component for processing the second electrical signals and first transmittable electrical signals 205 into signals that are configured for being received by the cochlea of a user's second ear, for facilitating the hearing of sounds that would be received by both of the user's first 12 and second 16 ears wherein the only functionally hearable sounds received by the user's ear 16 are generated through the second hearing member 208 for broadcast to the good ear 16.

As best shown in FIGS. 8, 8A, and 8B, second hearing aid 208 includes an externally disposed component 212 and an internally disposed component 214. In practice, the externally disposed component 212 is worn on the outside of the user's head and the internally disposed component 214 is implanted under the user's skin, and ultimately into the interior of the cochlea.

The externally disposed component 212 includes a housing member 218 that includes a first transducer 232, a first signal processor 234, and a signal alteration processor 236, which may also include an indicia signal processor as a part thereof for sending a signal to actuate a nonaudible signal such as a tactile or light signal. The housing member 218 has a coupler 220 for helping to couple the housing in 218 to a user's body part such as his ear 16. Coupler 220 and housing member 218 are designed and configured to be similar in configuration to a commercially available speech processor of the type that one wears, wherein the housing member 218 is disposed behind the ear pinna.

A wire conductor 222 is provided for conducting signals between the housing member 218, and the subcutaneously positioned scalp-attached member 224. The under-scalp-attached member 224 includes a transmitter 226 for transmitting signals transdermally that can be received by the internally disposed receiving antennae 244. The underscalp-attached member 224 also includes an external magnet 228. The externally disposed component 212 preferably includes a first magnet for magnetically coupling the external component 212 to the subcutaneously disposed internal member 224, which includes its own magnet. The external component 212 also includes a coil which electrically communicates power and information signals to a corresponding coil of the internal member 224.

The first transducer 232 preferably comprises a microphone type device and is provided for receiving sounds that would be received by the user's ear 16 and converting the received sounds into second electrical signals.

A receiver that comprises a first signal processor 234 is provided for receiving the first transmittable signals 205 and second electrical signals received by transducer 232, and the processing of those signals so that they are configured to be received by the cochlea of the user's ear 16. A second alteration processor 236 may comprise a part of the first signal processor 234, or may be a stand-alone unit as shown schematically in FIG. 8C. The signal alteration processor may include an indicia signal processor, or otherwise include a signal processor for conveying a signal to an indicator device such as a light or vibrator.

The signal alteration processor 236 is provided for altering one of the first transmittable electrical signal and second electrical signal so that the user can hear the difference between sounds received by the first hearing aid member 206 and sounds received by second hearing aid member 208 to permit the user to distinguish between the sounds received by the first hearing aid member 206 and sounds received by the second hearing aid member 208 to aid the user in achieving a sense of the direction of origin of the sounds being input into the second ear 16.

This alteration can take one of many forms. For example, the "altered signal" can be altered and processed so that the altered signal has distinguishably different sound characteristics when the electrical signals are processed to include the alteration artifact. These different sound characteristics, when transmitted out of the electrodes 252, cause the hairs of the cochlea to perceive that the "sound" being induced by the electrodes 252 is different and altered from the sounds being produced by the electrodes as a result of the unaltered signal.

There are many ways in which the sound can be altered. For example, the alteration signal can comprise a change to the altered sound so that it has a change in pitch, so that an echo is induced so that the signal is delayed so that the signal is filtered, or chorus effect is added. Additionally, the signal can be altered by attenuating different frequency bands, resonating the signal, or adding an artifact to the signal. Further, the altered signal can have its strength altered to alter its volume. A humming sound can be induced including a vibration type humming, or a tone can be added as a signal. Additionally, the signal can be modulated.

The above-discussed signal alterations performed by the second signal alteration processor 236 all relate to alterations in the sound transmitted through the cochlear implant into the cochlea hairs. As an alternative, the alteration processor 236 can generate a non-produced sound producing indicia member that is configured for providing one of a tactile or visual indicator to the user to aid the user in achieving a sense of direction of origin of the sounds being input into the second ear 16. Conceivably, this alternative signal could also comprise an olfactory and/or taste-based indicator through the chorda tympani nerve.

As will be discussed below, this device for generating the indicator can be a vibratory member that is configured for emitting a vibratory signal of variable intensity that can be felt by the user. The signal produced can be a variable signal that can be made less or more intense, with the intensity being correlated with the volume of the particular sound signal that is received by the transducer.

As an alternative, the signal produced by the alteration transducer 236 can be transmitted by wire or wirelessly to a first light for providing a usual signal of variable intensity that can be seen by the user, that correlates with one of the first and second sound signal received by respectively, the first 12 and second ear 16.

A second light providing member can be employed similarly. In such a case, one would have a first and second light indicia that would be positioned, respectively on a first and second body side, such as a left and right wrist, with each of the first and second lights being capable of having a light variable intensity that can be seen by the user, with the intensity of the light being correlated to the relative sound strength of the particular first and second signals. For example, if the user had a first light on his left wrist and the second light on his right wrist, and if the sound being produced in the user's left side had twice the intensity of the sound received on the user's right side, the light on the user's left wrist would be configured to have an intensity that possibly could be twice as bright as the intensity of the light on the user's right wrist.

All of the various alteration vehicles, including both audible and non-audible alteration vehicles are all believed to be highly useful in the present invention with persons who have an asymmetric hearing loss, and more particularly, for persons having asymmetric hearing losses characterized by the hearing in the "bad ear" being sufficiently profound so that hearing in the "bad ear" is incapable of being substantially restored with an amplification adjustment type hearing aid.

As best shown in FIGS. 8A, 8B, and 8C, the internal portion 214 of the hearing aid includes a receiving antenna 244 that is capable of receiving signals transmitted by the transmitting antennae 226 of the external hearing aid member 212. An internal magnet 246 is alignable with the external magnet 228, so that the external magnet can transfer power to the internal magnet and battery through magnetic charging to provide recharging for a power source such as a battery for operating the internal hearing and member 214.

The internal portion also has a signal processor 244 to process the signals received by the receiving antenna 244, and a signal conductor 250 that extends through the interior of the body to the cochlea. The distal end portion of the signal conductor 250 is inserted into the cochlea, with the extreme distal ends comprising an electrode array 252 for transmitting electrical signals to the hairs of the cochlea which comprise the receiving cilia that are capable of receiving electrical signals from the interior of the cochlea and transmitting those signals to the hearing centers of the brain.

As best shown in FIG. 8C, the first hearing aid member 203 includes a first transducer 204 that serves as a microphone for picking up sounds that are received along the first side of the user's body. Preferably, the first hearing aid member 203 is placed adjacent to the first ear 212, so that the sound received by transducer 204 approximate sounds that would be received by the ear 12 if the ear were functioning.

The first hearing aid 203 may also include a first signal processor 211 and a second signal processor 213 that are configured for processing signals received by the transducer 204. Either the first or second signal processor 211, 213 can comprise an alteration processor to alter the signal received by the first transducer, in lieu of the use of signal processor 236 that is part of the second hearing aid member 208. The processed signal 205 is then transmitted from the first hearing aid member 203 to the second hearing aid member 208.

Although the invention has been described with reference to certain detailed embodiments, it will be appreciated that variations and modifications exist within the scope and spirit of the claims as appended hereto.

FIG. 9 shows an alternate embodiment asymmetric hearing aid system 268 that includes a non-audible indicia that can be used in addition to, or in lieu of, an audible indicia such as the tone addition discussed above.

The asymmetric hearing aid system 268 shown in FIG. 9 includes many of the same components that are shown in the asymmetric hearing aid system 200 that is shown in FIG. 8C. However, in addition to the components shown in asymmetric hearing aid system 200 of FIG. 8C, asymmetric hearing aid system 268 includes a pair of vibrator members, including a first vibrator 270 that is placed on the same side as the user's "bad ear" 12, and a second vibrator 272 that is placed on the same side of the head as the user's "good ear" at 16.

A communication system, which can be wired or wireless, extends between the transducers 213, 236 of the first and second hearing aids 203, 234 to communicate signals from the first and second hearing aid members 203, 208 to the vibratory members 270, 272 respectively. The vibrating members operate in a manner wherein they will induce a vibration, to help indicate the direction of original of the particular sound that is being heard is originating to thereby enable the user to gain some sense of directionality with regard to the origin of the signal.

The vibrators 270, 272 are preferably either placed subcutaneously on different sides of the user's head, or alternately, can be positioned adjacent to the ears 12, 16 of the user's subcutaneously. As an alternate embodiment, the hearing aid vibratory members 270, 272, can be coupled to and made a part of the first 203 and second 208 external hearing aid housings that are carried on the user's ear so that they do not need to inserted subcutaneously on the user. By placing the vibrators 270, 272 on this part of the outer casing members, one would also presumably make battery replacement much easier and quicker.

In operation, sound that originated from the "bad ear" 12 side of the user's head would likely cause the signal to be generated to cause a vibration of the first vibrator member 270 so that the user would know that the sound originated from the "bad ear" 12 side of his head. Similarly, if the sound originated from the "good ear" 16 side of the user's head, the second vibrator 272 would vibrate, so that the user would know that it was coming from the right side.

As an example, imagine the user standing on a street and a car crashes causing a loud noise on the right side of the user. In a prior asymmetric hearing device, the user would hear the crash, but as only a monaural signal was fed to the user, the user would not be able to determine whether the crash noise that he was hearing through his "good ear" 16 actually originated from his good ear 16 side or his "bad ear" 12 side.

With the present invention, the intensity of the sound coming from the users "good ear" 16 side would cause the "good ear" 16 side vibrator 272 to vibrate, or to at least vibrate with a greater intensity than the "bad ear" 12 vibrator 270. This difference in vibration would enable the user to recognize that the sound was coming from his "good ear" side 16 so that the user could turn to look to his right (his "good ear" 16 side) to observe the crash and, if necessary, take evasive action to avoid being injured by the crash or its aftermath.

Another example of the asymmetric hearing aid of the present invention serving the user involves a situation wherein a person is at a meeting or gathering of some sort. For many hearing-impaired persons, their understanding of the conversation around them is often supplemented by an ability to read lips. In a typical meeting, sounds may be coming from various persons who may be seated around a conference table.

With the asymmetric hearing aid of the present invention, the direction from which the speaker's sound was originating, would likely cause one or both of the vibrators 270, 272 to vibrate at different intensities. Because of the relatively different intensities of the vibration, the user would have a clue as to which direction to turn his head to face the speaker who is speaking. For example, if the greater intensity of vibration was emanating from the first or "bad side" vibrator 270, the user would be cued to turn his head to the left to look at the speaker and thereby enable himself to read the speaker's lips. Similarly, if the speaker was sitting on the user's right, the relatively more intense vibration of vibrator 272 would cue the user to look to his right. If the vibration of the two vibrators 270, 272 was about equal, the user would be cued to either look straight in front of him or straight behind him as the equal vibration between the two vibrators 270, 272 would signal that the speaker was either directly in front or behind the user.

It should be understood that the vibrators 270, 272 are capable of vibrating at different intensities and that the intensity of vibration of a particular vibrator 270, 272 should be proportional to allow the sound being received at a position adjacent to where the transducers 204, 232 are positioned, which are preferably positioned adjacent to the user's "bad ear" 12 or "good ear" 16 respectively.

The vibrators 270, 272 should vibrate independently of each other so that the vibration of the first vibrator 270 can be differentiated from that of the second vibrator 272 not just by position but also by intensity.

In an alternate situation, one can imagine having two different speakers with one speaker being a louder speaker positioned on the user's "bad ear" 12 side and the more soft-spoken speaker being positioned on the user's "good ear" 16 side. Because of the difference in intensity of the volume level of the speakers, the vibration that would be imparted to first vibrator 270 would likely be more intense, because the speaker on the "bad ear" 12 side was speaking at a higher volume, whereas the vibration imparted to second vibrator 272 would be less intense because the speaker on the "good ear' 16 side was speaking at a lower volume level.

An alternate embodiment hearing aid member that is usable with the asymmetric hearing device of the present invention is shown in FIG. 10. Hearing aid component 278 is shown as a typical externally hearing aid device, that may be configured in a manner similar to any of the hearing aid devices discussed herein above. Device 278 comprises an externally worn component that includes a body 280 having a coupler 282, which is configured so that the member can be worn over the user's ear.

The internal circuitry of the device 278 can be configured as necessary, in accordance with the teaching contained herein.

The external hearing member 278 includes a tactile sensory indicator, here shown as vibratory indicator 284. Vibratory indicator comprises a vibrator to induce a tactile sensation in the user. As the device 272 is worn against the user's head, the tactile indicator will induce a tactile sensation on a side of the user's head close to a user's ear. The external device 278 shown in FIG. 10 should be used in pairs with one such device being placed over the user's bad ear and a second device placed over the user's good ear 16. It will be appreciated that the internal components and function of the hearing aid device 278 that is placed over the bad ear will differ from the components and function of the device placed over the good ear 16, with the differences being designed to be in accordance with the teachings of the asymmetric hearing aid device contained herein.

FIG. 11 comprises an alternate embodiment hearing aid device 290 that may include one or both of tactile and light-based indicators. The ultimate asymmetric hearing aid 290 includes a first hearing aid member 292 disposed adjacent to the user's bad ear 12, and a second hearing aid member 294 disposed adjacent to the user's good ear 16. A signal 295 is transmitted from the first hearing aid member 292 to the second hearing aid member 294. The hearing aid members 292, 294 include signal processors, which may include an alteration signal process in a manner similar to the hearing aids discussed above, such as hearing aid system 268 disclosed in FIG. 9, and hearing aids 10 discussed in FIG. 3 et seq.

A pair of eyeglasses 262 comprise a component of the asymmetric hearing aid device 290. The eyeglasses include first and second 298, 299 secondary indicator members, which are disposed respectively on the left and right side of the eyeglass members, to induce an indicia close to the left and right sides of the user. The indicia, be a light or tactile that is imparted to the eyeglasses should be spaced far enough apart, so that the user can easily distinguish between the sensation induced by the first indicator 298, and the sensation induced by the second indicator 299. The eyeglasses 262 can also include first 356 and second 358 tactile indicators disposed on the first and second sides of the nose engaging portion of the glasses, as is described in more detail below in connection with FIGS. 13 and 14.

The first and second indicators 298, 299 comprise lights for inducing a light-based indicator to the user. Alternately, first and second indicators can comprise vibrator members to induce a tactile sensation onto the user.

The tactile sensation that is induced by the first and second indicator should be indicative of the direction of sound from which a signal originated. As such, if the sound originated from the left of the user, the indicator 298 would induce a sensation to the user. Conversely, if a sound originated from the right side of the user, the second indicator 299 would induce a sensation onto the user, be a light-based sensation or a tactile-based sensation. It will be appreciated that in many situations, the sound will come from both the left and right side of the user although the intensity of the sound from the left side of the user will differ from the right side of the user.

As a hypothetical, one can image a situation where one is standing next to a railroad track, and a train is arriving on the track from the right side of the user. Although the predominant amount of sound will be originating from the right side of the user, the sound will likely also be intense enough so that the sound of the train will be received by the left side of the user.

The device 290 shown in FIG. 11 is configured so that in such a situation, the second sensation imparting device that is placed on the user's right, would be configured to send a more intense light or vibrational signal to the user, than the first sensation inducing member 298 that is disposed on the left side of the user, wherein the sound that is picked up by the transducer of the left side of the hearing aid 292 would be less intense than that picked up by the right side hearing aid 294 transducer.

FIG. 12 comprises another alternate embodiment hearing aid device 304 that includes a tactile indicator that is configured as a necklace 312 having a band 314.

The asymmetric hearing aid system 304 of FIG. 12 includes a first hearing aid member 306 and a second hearing aid member 308. The first hearing aid member 306 is capable of transmitting a signal 310 from the first hearing aid member 306 to the second hearing aid member 308. The first and second hearing aid member 306, 308 are preferably configured in accordance with the teachings of the first and second hearing aid members discussed above in connection with devices such as hearing aid device 200 of FIG. 8 and hearing aid device 10 shown in FIG. 3 et seq.

The hearing aid system 304 of FIG. 12 includes a tactile indicator member 312 that is shown as a necklace 312 and includes a band 314, that can rest on the neck and shoulders of the user. The band 314 includes a receiver member 316 which can receive a signal that is transmitted to it. A signal 315 can be transmitted from the first hearing aid to represent sounds picked up by the transducer of the first hearing aid 306; and a second signal 317 can be transmitted from the second hearing aid 308 to represent sounds picked up or received by the transducer/pick-up of the second hearing aid 308.

Alternately, a single signal can be transmitted from one of the first and second hearing aid members 306, 308. The signal transmitted from the hearing aids to the tactile members should have directionality components so that the signal received by the receiver 316 can be transmitted to one of the first 318 second 320 third 322 and fourth 324 tactile indicator members that induce a sensation in the user.

It will be noted that the first tactile indicator 318 is placed on the user's left side, the second tactile indicator 320 is placed on the user's right side, the third tactile indicator 322 is placed on the user's front side, and the fourth tactile indicator 324 is placed on the user's read side. Each of the tactile indicators should be variable in nature so that they can impart a sensation of variable strength.

In operation, the sound received by the first and second hearing aids 306, 308 is processed so that the signal is converted into one that correlates to intensity. In a most preferred embodiment, each of the first and second transducers 306, 308 comprise a pair of transducers, with one located to pick up sounds in front of the user, and with a second being located to pick up sounds behind the user. As such, the two transducers that might be coupled to first hearing member 306 can be placed on the front surface of the hearing aid to pick up sounds that originate more from the front and left side of the user, with the second transducer being placed on the rear of the hearing aid device 306 to pick up sounds that are picked up on the left and rear of the user.

Through the use of these four transducers, signals can be generated wherein the intensity of the signal that is sent to the received 316 has the capability of imparting a directionality that is relative not only to the left and right side of the user, but also to the front and rear of the user. The intensity related that is transferred to the receiver 316 can then be transmitted to the respective tactile indicators 318, 320, 322, and 324 provide a directionality to the user that includes both side to side and front to back components.

In a hypothetical situation, imagine a user standing on a street, wherein a cross street exists 40 feet in front of the user. On this cross street is a fire truck that is driving in a direction from the user's left to the user's right.

The tactile indicator of the present invention in such a case, would cause the front 322 and left 318 tactile indicators to induce a sensation on the user that is relatively greater than the sensation induced by the rear 324 and right side 320 tactile indicator. Through this difference in intensity, the user would be given a sensation that would indicate to the user that the noise making device (here the fire truck) that the user was hearing through the hearing aids 306, 308 was originating from in front of and to the left of the user.

As the fire truck passed by (assuming the user did not continue to walk farther), the intensity level imparted by the left tactile indicator 318 would continue to decrease with the tactile sensation imparted by front tactile indicator 322 increasing, and reaching its maximum at a point when the fire truck was directly in front of the user. As the fire truck continued to cross the intersection and move on to the right, the intensity imparted by the left side indicator 318 would continue to decrease, as would the sensation imparted by the front indicator 322. Concurrently, the tactile sensation indicated by the right tactile indicator 320 would continue to increase in intensity as the truck continued to move to the right, and the primary sound being generated from the truck became positioned more to the right of the user, and less to the front of the user.

Turning now to FIG. 13, a non-audio producing indicator is shown which in FIG. 13 comprises a pair of eyeglasses 330. Eyeglasses 330 have a front piece 332 that includes a first lens 334 that is placed over the user's first (left) eye, and a second lens 336 that is placed over the user's second (right) eye. A nose engaging member 338 includes a first nose engaging portion 340 for engaging the left side of the user's nose, and a second nose engaging portion 342 for engaging the right side of the user's nose.

Eyeglasses 330 also include first and second temples 346 350, that are hingedly mounted to the front piece 332. The first temple 346 includes a first ear engaging portion 348 that is disposed at the distal end of the first temple 346. The second temple 350 also includes a second ear engaging portion 352 that is disposed at the distal end of the second temple.

The eyeglasses 330 include a tactile sensation generating indicator. The tactile sensation generating indicator includes a first tactile indicia generator 356 that is positioned on the first nose engaging member 340 to provide a tactile sensation to the left side of the user's nose; and a second tactile sensation indicia generator 358 that is disposed on the second nose engaging portion 342 for imparting a tactile sensation to the right side of the user's nose. Preferably, the tactile sensation that is induced by the two generators 356, 358 comprises a sort of vibratory sensation which alerts the user to the presence, without tickling his nose in an annoying manner.

Third and fourth tactile sensation indicia generators 360, 362 are disposed on the distal end of the first and second temple 346, 350 and are positioned to impart a vibration to the place where the tactile sensation indicia generators 360, 362 engage the ear flap of the user on the side of his head.

Another alternate embodiment of a pair of eyeglasses 364 is shown in FIG. 14 that includes both tactile and light non-audio generating indicators. The tactile non-audio generating indicators 356, 358, 360, 362 are generally similar to the ones shown in FIG. 13. The light non-audio generating indicators are not shown in FIG. 13, and include a first light indicia generator 370 that generally comprises a plurality of lights disposed on or above the first or left lens 374, and a second light indicia generator 372 that comprises a similar plurality of lights disposed on or above the second lens 336.

The light indicia (as are the tactile indicia) are in communication with the hearing aid members discussed above. When sound is produced that originates on the user's left side (bad ear side 12), the first lens lights 370 will be illuminated to indicate to the user that the sounds are coming from the user's left side. In contrast, if sounds are originating from the user's right side, the lights 372 of the second light indicia generator will be illuminated to indicate to the user that sound is originating from the right side of the user's body.

There are many ways that the lights can be tailored to provide more precise information. For example, as it will be noticed, there are a plurality of lights in each of the first and second light indicia generators. The outboard most light 376 is positioned adjacent to the intersection of the front piece 332 and the temple 346. The inboard most light 378 is positioned closest to first lens 34 but is positioned generally above the nose piece 338 in the center portion of the front piece 332 of the eyeglasses 364. Similarly, a plurality of lights exist between the outboard most light 382 of the second light generating indicia 372 and the inboard most light 384 thereof.

To help better define where the sound is coming from, the lights can be designed to be individually actuable. For example, if the sound is coming from the user's extreme left side, it is possible that only outboard-most light 376 and possibly the next one or two adjacent lights would be lit. On the other hand, if the light is coming from the front of the user, it is possible that lights 378, 384, and the lights adjacent thereto would be lit.

Another vehicle for providing more precise information is to illuminate a variable number of lights or to vary the intensity of the light so that the user can get an indication of the relative strengths of the sound.

As discussed above, if the user was standing adjacent to a train track and an ongoing train was approaching from his left side, audio signals would be picked up by both the transducers of the hearing aids on the user's bad ear side 12 and good ear side 14. Nonetheless, if the train was coming from the user's left, the greater intensity of the sound would be coming from the user's left side and be picked up by the transducer over the user's bad ear side 12. In such a situation, more lights could be lit up in the first light indicia generator 370 than the second light indicia generator 372 to tell the user that the majority of the noise was coming to the user's left side.

Alternately, the intensity of the lights on the first light indicia generator 370 could be much brighter than the lights of the second indicia generator 372 to provide an alternate indication to the user that the "big sound" produced by the oncoming train was coming from the user's left side. In an alternate embodiment shown in FIG. 16, the lights of the eyeglasses 388 are grouped schematically in groups of three, here shown as first, second, third, fourth, and fifth groups, 390, 392, 394, 396, and 398. Each of the groups comprise one or more red lights, green lights, and blue lights. Through the use of this "RGB" array, different colors can be formed. As such, in the embodiment 388 shown in FIG. 16, the lights can change color depending on intensity and direction.

For example, if a relatively softer sound originated from the user's left side, the lights of the first group 390 could be illuminated to produce a blue signal, which would indicate to the user that the sound was originating from his left side (due to the illuminating of group 390) and that the sound was at a low volume, as indicated by its blue color. Alternately, if a very loud sound was originating from the user's right side, light group 398 could be illuminated to show a red light. In this case, the fact that group 398 was being lit would indicate that the sound was coming from the user's right side, and the fact that group 398 was being illuminated in red would suggest the sound was loud.

Another variation on this theme would occur in a situation where a hypothetical loud sound was originating directly in front of the user. In such case, the center RGB display grouping 394 would be illuminated red to indicate that the strongest audio signal was coming in front of the user, with the relatively outboard groups 392, 396 being illuminated in a color such as green or yellow to suggest that an intermediate noise level being produced at, for example, a 45-degree angle to the user's head, with blue light being generated from the farthest outboard displays 390, 398 to indicate that only a small portion of the sound's intensity was originating from either the left or right of the user.

A processor contained within the earpiece of the hearing aid would likely be employed to process and measure the relative sounds being heard from the first and second hearing aids to thereby make a determination as to the direction of origination of the sound.

FIG. 15 shows an alternate embodiment pair of eyeglasses 400, wherein the first and second light indicia generators 402, 404 are shown as signal light sources which would be illuminated or turned off depending upon the origination of the sound being heard by the user. It will be appreciated that the intensity of the light emitted by light generating indicia 402, 404, could be varied to better correlate with the intensity of the sound.

FIG. 17 shows an alternate embodiment pair of eyeglasses 407. Although the eyeglasses 407 of FIG. 17, et seq., do not show a set of tactile indicia generators, it will be appreciated that the tactile indicia indicators discussed in previous figures can be used in connection with these embodiments. The embodiment of FIG. 17 has a first 405 and second 406 row of light indicia generators. This embodiment is designed to illustrate that one of the rows (e.g. first row 405) can be used for giving indications of the direction of sound with the other row (e.g., second row 406) being used to indicate the intensity of sound.

Another embodiment pair of light indicia generating eyeglasses is shown in FIG. 18 wherein the light indicia generators generate light around the perimeter of the front piece of the frame. An array such as this would be used to help indicate to the user a "360 like" indicator sound origination. In such case, the top row of lights 409 could be used to indicate left and right direction, with the bottom row of lights that extend around the lower edge of the eyeglasses 408, and the bottom of the lenses and the nose piece are used to indicate whether the sound was coming predominantly from in front of the user or behind the user.

FIG. 19 shows an eyeglasses embodiment 412 that includes a screen surfaces 413, 414, wherein display information can be projected into the lens for viewing by the user. For example, it would be possible that something such as a "compass" type icon could be projected or generated into the eyeglasses 412 lenses 413, 414 to allow the user to know whether the intensity of the sound is coming from in front him, to the side of him, or behind him. Additionally, various colors could be employed to indicate various directions of the sound origination. These colors may be different colors that indicate intensity and direction similar to the colors employed on a TV newscast to illustrate different storm intensities, and different weather conditions.

FIGS. 19A, 19B, and 19C relate to an alternate embodiment non-audio indicia generator that employs a mobile smart phone 437 to generate the non-audio indicia. Although the indicia discussed below are primarily visual in nature, it will also be understood that it may be possible to use a tactile indicia such as a vibrational indicia. However, it is believed that a visual indicator has advantages at the present because of the significantly greater power of a mobile phone to display things visually, in a directional manner, when compared to vibrationally.

The cell phone 437 shown in FIG. 19A comprises a typical smart phone type mobile telephone which would be operated by a suitable application that would be able to communicate between the mobile phone and a processor 445. Although the mobile phone would certainly require its own processing capabilities, the processor 445 could be a part of the hearing aid system. Similar to the device shown in FIG. 30, the processor 445 might be designed to process signals received from either a plurality of microphones (e.g., microphones M1-M8) or if from a first and second transducer, or from a variety of user-worn transducers, such as four transducers that might be placed on each of the user's front side, rear side, left side, and right side. The purpose of the processor 445 is to process the sounds received from these multiple transducers in a manner that creates an output that is indicative of the direction or origin of the sound.

Because of the relative positions of the various transducers that pick up the sound, the sounds picked up by the various transducers will all have different sound intensity contributions, which can be processed to provide the user with a general indication via the cell phone of the direction and intensity of the origination of the sound.

As shown in FIG. 19A, a directional field image 443 is displayed on the phone screen 441. The field image 443 includes crosshairs, having the user at the center. Additionally, indications are provided to apprise the user of his relative right side R, left side L, front F, and back B.

Displayed on the screen are three exemplary indicia including a first displayed indicia 451, a second display indicia 453, and a third display indicia 455. The indicia 451, 453, 455 are positioned to represent the origination of a sound. For example, the sound that generated the first displayed indicia 451 would indicate that the sound is being generated relatively close to the user, and to his front and right side.

Similarly, the second displayed indicia position 453 would indicate that the sound being generated by the second display indicia 453 was being produced at a further distance from the user and on his left side. The third display indicia 455 would indicate that the sound is being generated from somewhere behind the user.

At a most preferred embodiment, the processor 445 would be able to generate the display indicia based upon being able to distinguish between sounds, and then processing sounds similar to the distinguished sound, in a manner that relates to position, so that the display indicia 451 would not only relate to a large (loud) sound, but rather a large particular sound. For example, if the processor 445 were able to distinguish between a sound made by a first, male speaker, a second, female speaker, and a third, doorbell, the sound picked up by the transducer and processed by the processor might be able to indicate that the first displayed indicia 451 indicated the position of the first male speaker, the second display indicia 453 indicated the position of the second female speaker, and the position of the third indicia 455 would indicate the position of the doorbell.

In addition to positions, the displays could be designed to have a color that was representative of intensity of the sound. For example, indicia 451 might be colored yellow to indicate that the sound was of medium intensity, whereas the second indicia 453 might colored red to indicate that the sound had a greater intensity. Through this, the user could determine that the sound that the user heard (e.g., the loudly speaking woman) would correspond in position to the person on the user's left as indicated by the position of display indicia 453, and the loud-voiced speaker that the user was hearing as at position 455, by virtue of the red color of the indicia 453.

FIG. 19B represents an alternate embodiment comprising a novel modification of the device shown in FIG. 19A. The device in FIG. 19A comprises a second mobile phone 459 having a screen 441 and a processor 445 that are generally similar to those discussed in connection with cell phone 437 of FIG. 19A. Additionally, phone 459 screen 441 is shown as having displayed a first, second, and third indicias 467, 469, 471. The diamond-shaped indicia 473 that overlays the first displayed indicia 469 comprises not an indicia but a rather a controller button 473, as most mobile phones have touch screens, the user would be able to manipulate the controller button 473 to overlay one of the displayed indicia 467, 469, and 471 of the user's choice, to help the user isolate the particular sound being generated that relates to the particular display indicia 469, 471, or 473.

For example, if the user was hearing the two voices of two men, positioned at positions 467 and 469, the user might wish to place the control button 473 over indicia 467, to help isolate the sound being generated by man 467. By being able to isolate the sound, the user could then recognize his voice, and distinguish it from the second user 469, so that further words spoken by the two men would be able to be distinguished by the user based upon his ability to identify the particular sound of each particular speaker.

The third mobile phone embodiment 477 is another alternate embodiment. Similar to phones 437 and 457, phone 477 includes a directional field 481 having a first display indicia 483, a second display indicia 485, and a third display indicia 487.

Additionally, cell phone 477 includes a direction control 489, which enables the user to quickly toggle between, for example, left and right. In such a case, the user might, for example, simultaneously hear an oncoming car and an oncoming train. To better understand the position of the train and the car, the user might toggle the toggle switch 493 of the direction control 489 over to the right. In so doing, the sound generated from the right side, which would primarily from the display indicia 487, would increase in intensity.

If the sound that the user heard that increased in intensity was the sound of the train (as opposed to the sound of the oncoming car) the user would then be able to recognize that the train's position corresponded generally to the position of third display indicia 487, and was thereby originating from the user's right side. Similarly, by toggling the switch 493 over to the far left side, the intensity of the train sound would diminish, while the intensity of the car sound would increase, to indicate to the user that the car sound and, hence, the car was originating from the user's left side, as indicated by second display indicia 485.

To aid in this, an intensity gauge 485 could provide a visual clue to the user that related to the direction of intensity. As shown in FIG. 19C with the toggle switch 493 over to the right, the intensity of the sound would originate primarily from the user's right side, as shown in the three raised bars, with relatively less to no intensity being generated from the user's left side as indicated by no raised bars.

FIG. 20 shows another alternate embodiment pair of eyeglasses 416 wherein the lenses 334, 336 include a plurality of lights 417 so that directional indicators can be employed over a large portion of the first and second lenses 334, 336 in some array that is designed to convey directional information and possibly intensity information to the user.

FIGS. 21-26 show various annular, non-audio indicators, each of which includes a plurality of non-audio indicia generators thereon. In the devices shown, the primary indicia generators are tactile sensation indicia generators. The use of a plurality of such generators spaced in an annular array around the user or a user's body part, helps to give the user a better tactile indication of the direction of origination of the sound, both with regard to left and right origination, and also front to back origination.

FIG. 21 shows a collar 420 that can be worn around a user's neck includes a plurality of such tactile indicia generators 421 that are disposed in annular array along the length of the collar 420 and around the user's neck. In such case, a sound originating primarily from the rear of the user would cause the tactile indicia generators 421A that were disposed on the back of the user's neck at approximately 180 degrees from the collar's buckle 419 would induced a tactile vibratory sensation to indicate to the user that the sound was originating behind him. FIG. 22 shows a bracelet member 422, having a similar annular array of tactile indicia generators 423. The bracelet 422 can be used either by itself, or in combination with another bracelet (not shown). Used in a combination, the bracelet 422 on the user's left wrist would generate a tactile sensation if the sound was generating from the user's left side, and the bracelet on the user's right wrist would generate a tactile sensation if the sound was generating from the user's right side. When used alone, the tactile generators 423 would be configured similarly to those in the collar 420 so that a particular position of the tactile generator would bear some relation to the direction of sound origination.

FIG. 23 shows an anklet 426 annular member including a plurality of tactile sensation indicia generators 427, that in practice has a function similar to that of the bracelet 422.

FIG. 24 shows a watch embodiment 430 of the present invention that includes a annular array of tactile indicia generators 431 disposed on the watch and the watch band 432, and FIG. 25 shows an annular indicia generator being disposed on a belt and including a plurality of tactile indicia generators disposed around the length of the belt.

Generally, FIG. 26 shows the present invention as embodied into a hat 438, wherein the interior band 439 of the hat 438 includes an annular array comprising a plurality of tactile sensation indicia generators 440, which would operate in a manner similar to that of the collar 422 and other embodiments discussed above.

Turning now to FIG. 27, another embodiment is shown. The embodiment of FIG. 27 shows a hat 450 having a band portion 454. A plurality of microphone 452 are arrayed around the band 454, and are preferably equally spaced from each other. Each of the microphone 454 is designed to pick up a sound that corresponds generally to a sound that would be heard if an ear were placed at that position.

The sounds from the various microphones are fed as electrical signals to a processing unit, where they are integrated and processed to be directionalized. The sound generated signals are then converted into an output signal comprising a tactile or light or electrical type stimuli, by an indicator generator 440 such as one that may be shown in the hat 438 of FIG. 26.

Because of annular array of microphones/transducers 452, an annular array of tactile, visual, or electrical stimuli and/or indicia 440 can be provided so that a user can better determine the origin of the sound, since the indication given by the visual, tactile, or electrical stimuli should vary in intensity in a manner that correlates with the relative intensity of sound picked up by the similarly positioned microphone 452. As such, a variation of the embodiment shown in FIG. 27 would be the combination of the devices as shown in FIG. 26 and FIG. 27, wherein a plurality of microphone transducers are placed on the outer surface of the hat band 454, and a corresponding array of indicator generators 440 are placed on the inner surface of the hat band 454.

Another embodiment indicator system is shown in FIG. 28 that shows an indicator generator system that can be used as a part of the hearing aid system of the present invention. FIG. 28 is designed to provide electrical stimuli to a patient to aid the user in determining the direction of original of a sound. The indicator generating device 460 of FIG. 28 employs a subcutaneously implanted first 462 and second 464 stimulator, which are implanted on the respective first 466 and second 468 side of the user's head.

First 470 and second 472 magnetic transmitters/chargers are magnetically coupled to the respective first 462 and second 464 indicator generator. It will be noted that first and second magnetic transmitters/chargers 470, 472 are positioned outside of the user's head, adjacent to the first 470 and second 472 magnetically implanted stimulators. Although the magnetic stimulators 470, 472 can provide a tactile vibration to the user, they may also be capable of providing an electrical stimulation of the type which is noticeable, but not annoying. The outer disposed magnetic transmitters/chargers 470, 472 are preferably wired or wirelessly coupled to the transducer or processor of the hearing aid system to receive signals from the hearing aid system for transmission to the internally disposed stimulators.

FIG. 29, shows a cochlear implant-based electrical impulse indicia generating system 480. The electrical indicia generating system 480 includes a first external member 484 and the second, subcutaneously implanted member 486.

As discussed above in previous embodiments, the external member 484 may include some operational circuitry, and a magnet for magnetically coupling to the second subcutaneously implanted member 486. The first externally disposed member 484 can provide signals to the second member 486, along with being able to recharge the battery of the second subcutaneously implanted member 486 or to power it transcutaneously.

The second subcutaneously implanted member 486 includes an electrical impulse indicia generator 488. The purpose of the indicia generator 488 is to generate an electrical signal that can be felt, but that is not unpleasant, to help a user determine a direction of origination of a sound.

When the subcutaneously implanted member 486 is used in connection with one of the hearing aid devices discussed above, a signal from a transducer from the hearing aid member on the user's bad ear side will cause an electrical stimulation to be generated by second implanted member 486 and transmitted to the indicia generator 488 to provide an electrical stimulation to the bad ear side 12 of the user's head, to indicate that the origin of the direction of the sound picked up by the particular transducer is from the user's "bad ear side" 12.

A cochlear implant 491 is disposed on the user's "good ear side" 16, and includes an external member 492, and a second subcutaneously implanted member 496. The external member and implanted member 492, 496 can be generally similar to the external member 212 and implanted member 214 that are shown in FIG. 8b and similar to those devices 212, 214 include a cochlear implant electrode 498. However, implant 491 includes a second electrode 500, that is similar to the electrical impulse generating indicia generator 488, as it provides an electrical stimulation to the user's good ear side 16 to signal to the user that the sound is originating from the user's good ear side. The electrical stimulation provided by the indicia generators 488, 500 can be variable, to vary in intensity, wherein the intensity varies with the intensity of the sound picked up by the transducer. Alternately, a subcutaneously positioned vibrational stimulator may be used in place of the electrical stimulator.

Although the device of FIG. 29 is shown with a cochlear implant, it will be appreciated that an external member and subcutaneous member, similar to external member 484 and subcutaneously implanted member 486 can be used on the user's good ear side in place of the cochlear implant as might be the case where there is no need for a cochlear implant in the user's good ear side. Such a device could be usable either with a hearing aid type hearing system, or a BAHA (bone anchored hear aid) system, or a cochlear implant.

A universal indicia generator 502 is shown in FIG. 31. The universal indicia generator has the advantage of being a mass-producible, low-cost indicia generator that can provide the user with the freedom to place the generator at one of a variety of positions on his body, on an article of clothing, or an accessory item such as a watch or collar, or on a medical appliance such as a pair of eyeglasses. The universal generator 502 may be designed to generate an indicia that might be a tactile indicia, an electrical stimulation indicia, or a light-based indicia. The universal generator stimulation patterns would be governed by the hearing device in accordance with and to relate to the sound origination direction. Alternately, the generator stimulation patterns may be governed independently by the universal generators' own sensors.

A particular advantage of the universal generator 502 is that it would lend itself to "retrofit" applications. For example, the universal indicia generator 502 could be coupled onto an existing pair of eyeglasses 528, thus obviating the need for the user to purchase "specially designed" eyeglasses that already incorporate an indicia generator. As such, one could merely purchase the universal indicia generator 502, and couple it (them) to a pair of eyeglasses that the patient already owns.

The universal indicia generator 502 is shown as having a body 504 that includes a plurality of components therein for operating the device. These components are shown schematically in FIG. 31 as including a receiver 506 for receiving a signal from the hearing aid system; a signal processor 508 for processing the signal so received; a power source 510 for generating power for operating the components; and a signal generator 512.

The signal generator 512 provides a signal to an output generator 514 for generating an indicia. The output generator 514 can comprise of a tactile indicia generator, visual indicia generator, or an electrical stimulus generating indicia or possibly even an olfactory type generator. The body 504 includes an attaching surface 516 that may include an attaching member 518, that can comprise something such as tabs, tape, hook and eye fasteners, and the like. An outer surface 520 is also provided which is disposed in an opposed relationship to the attaching surface 516.

Indicia can be generated on one or both of the attaching surface 516 and outer surface 520. For example, a light indicia would likely be generated and displayed on the outer surface 520 since the attaching surface 516 would likely be coupled to a user's body part or the like. On the other hand, a tactile or electrical stimulation generator would likely be disposed on the attaching surface 516, so that the vibratory or electrical stimulation could be directly conducted to the user.

FIG. 33 shows that the universal generator 502 can be worn by a user in a variety of ways to generate an indicia that helps the user better determine the origination of the sound. For example, universal indicia generators 524 are provided that are coupled to the side of the user's neck; generators 526 are coupled to the user's shoulders; generators 528 are coupled to the user's thigh; and generators 530 are coupled to the user's feet. Further, generators 532 are shown as being coupled to the user's hand. Obviously, it is likely that one particular user would not employ all of the various generators 524-532 discussed above. Rather most users would use only one or possibly two pairs of generators and would position them somewhere that would be most comfortable and convenient for the user/patient.

In addition to the generators discussed above, other generators exist that can be coupled to a user's article of clothing, rather than directly coupled to the user's skin. For example, generators 534 can be couple to a user's shirt, and generators 536 can be coupled to a user's watch band. Generators 538 can be coupled to a user's belt, as described in connection with the various bands and belts in FIGS. 21-23, generators 550 can comprise a plurality of annularly arrayed generators to give the user a "360 degree" stimulation. Generator 524 can be coupled to an ankle bracelet, similar to ankle bracelet 426 of FIG. 23.

As stated above, one of the benefits of the universal generator is that it can be coupled to an already existing article of clothing, such as an already existing belt, shirt, ankle bracelet, or wristwatch band or wrist bracelet. Although not shown, the universal generator can also be coupled to a necklace or collar.

FIG. 30 relates to a specially outfitted room 548 or space, such as a conference room or living room or kitchen that is designed to help a patient P with indicia generators that can help provide the user with information about the direction of indicating of the sound. Room 548 would preferably be the type of room in which the patient P would spend a large amount of time to help justify the expense of specially adapting a room.

The room is provided with a plurality of microphones M1, M2, M3, M4, M5, M6, M7, and M8 that are strategically placed around the room 548 to pick up sound from various locations of the room 548.

As discussed above in connection with the use of a plurality of microphones, the microphones M1-M8 are designed to pick up sound, and transmit the sound to a processor, which then processes the sounds received by the microphones in a manner that is indicative of the direction of origin of the sound. Through the hearing aid system of the present invention the processed sounds picked up by the microphone M1-M8 provides an indicator to the patient in a manner that takes the sounds received by the various microphones M1-M8 and provide a signal to the user that enables him to better determine the origin of the sound.

For example, in the room shown in 480 there are three speakers, S1, S2, and S3, which may represent three different people. Because of the relative positions of the speakers S1-S3 and the microphones M1-M8, the sounds picked up by the various microphones will all have different sound intensity contributions from speakers S1, S2, and S3. By appropriately processing the sounds, the user, for example, can receive a generated indicator of either a tactile, light, electrical or possibly olfactory nature that indicates to the user the direction of origin of the sound emanating from speaker S3. Similarly, the different position of speaker S1 causes the indicator signal produced and delivered to the patient P to be positioned differently on the patient P than the signal provided as a result of the sound originating from speaker S3.

Having described the invention in detail with respect to certain preferred embodiments, it will be appreciated that variations and modifications exist within the scope and spirit of the invention.

What is claimed is:

1. A hearing aid apparatus for use with a user having a first ear and a first body side on which the first ear is disposed, and a second ear and a second body side on which the second ear is disposed, the hearing aid apparatus being configured for enabling the user to hear sounds that originate from a plurality of directions, the hearing aid apparatus comprising:
a first hearing aid member placeable on a user's body on the same side of the user's body as the first ear, the first hearing aid member including a first transducer for receiving sounds that would be received by the user's first ear and converting those received sounds into first transmittable electrical signals,
a second hearing aid member placeable on the user's second body side, the second hearing aid member comprising a cochlear implant device including an electrode array positionable within a cochlea of a user, the cochlear implant device including a second transducer for receiving sounds that would be received by the user's second ear, and converting the received sounds into second electrical signals, a receiver for receiving the first transmittable electrical signals, and a first signal processor for processing the second electrical signals and first transmittable electrical signals into signals configured for being received by the cochlea of user's second ear for facilitating the hearing of sounds that would be received by both of the user's first and second ears, wherein the only functionally hearable sound signals received by the user's ear are generated through the second hearing aid member.

2. The hearing aid apparatus of claim 1 further comprising a signal alteration processor for altering one of the first transmittable electrical signal and second electrical signal so that the user can hear differences between sounds received by the first hearing aid member and sounds received by the second hearing aid member to permit the user to distinguish between sounds received by the first hearing aid member and sounds received by the second hearing aid member to aid the user in achieving a sense of the direction of origin of the sounds being output into the second ear.

3. The hearing aid apparatus of claim 2 further comprising a second signal processor, the second signal processor including the signal alteration processor, the second signal processor being configured for processing at least one of the first transmittable electrical signal and second electrical signal to have distinguishably different sound characteristics when converted from electrical signals to sound signals.

4. The hearing aid apparatus of claim 2 wherein the signal alteration processor is contained on at least one of the first and second hearing aid members, and wherein the second signal processor processes the at least one of the first transmittable electrical signal and second electrical signal to alter the signal by at least one of changing its pitch, inducing an echo, delaying the signal, filtering the signal, adding a chorus effect, attenuating different frequency bands, resonating the signal, adding an artifact to the signal, changing the strength of the signal to alter its volume, inducing a humming sound, inducing a vibration, adding a tone and modulating the signal.

5. The hearing aid apparatus of claim 2 wherein the signal alteration processor processes the one of the first transmittable electrical signal and second electrical signal, by altering the processed signal to generate a non-sound producing indicia member in communication with the signal processor configured for providing one of a tactile or visual signal to the user to aid the user in achieving a sense of direction of origin of the sounds being output into the second ear.

6. The hearing aid apparatus of claim 1 wherein the hearing aid apparatus comprises a hearing aid apparatus configured for providing directionality of sound origination to a user having a first ear having a hearing loss sufficiently profound that a normal approximately symmetric hearing condition is incapable of being substantially restored with an amplification adjusted hearing aid.

7. A hearing aid apparatus for use with a user having a first ear and a first body side on which the first ear is disposed, and a second ear and a second body side on which the second ear is disposed, the hearing aid apparatus configured for enabling the user to hear sounds that originate from a plurality of directions, the hearing apparatus comprising:
a first hearing aid member placeable on a user's body on a user's first body side, the first hearing aid member including a first transducer for receiving sounds that would be received by the user's first ear and converting those received sounds into first transmittable electric signals;
a second hearing aid member placeable on a user's second body side, the second hearing aid member including a second transducer for receiving sounds that would be received by the user's second ear and converting the received sounds into second electrical signals, a receiver for receiving the first transmittable electrical signals, and a first signal processor for processing the first transmittable electrical signals and the second electrical signals into signals configured for being received by the user's second ear for facilitating the hearing of sounds that would be received by both of the user's first and second ears, wherein the first signal processor includes a signal processor for processing one of the first transmittable electrical signal and second electrical signal, and a non-audio producing indicator member in communication with the signal processor configured for providing non-audio signal to the user to aid the user in achieving a sense of direction of origin of the sounds being output into the second ear.

8. The hearing aid apparatus of claim 7 wherein the indicator member comprises a first vibratory member positioned on the first body side of the user, the first vibratory member being configured for emitting a vibratory signal of variable intensity that can be felt by the user, and a second vibratory member positioned on the second body side of the user, the second vibratory member being configured for emitting a vibratory signal of variable intensity which can be felt by the user.

9. The hearing aid apparatus of claim 8 further comprising a sound intensity controller for comparing the relative volume of sound received on the user's first side with the volume of sound received on the user's second side, and generating a signal to each of the first and second vibratory members for causing the first and second vibratory members to emit vibratory signals that correlate in intensity to the respective volumes of sound received on the user's first and second side.

10. The hearing aid apparatus of claim 7 wherein the indicator member comprises a first light producing member positioned on the same side of the user as the first ear, the light producing member being configured for emitting a first light signal of variable intensity that can be seen by the user and a second light producing member positioned on the same side of the user as the second ear, the second light providing member being configured for emitting a second light signal of variable intensity that can be seen by the user.

11. The hearing aid apparatus of claim 7 wherein the hearing aid apparatus is configured for providing hearing to a user whose first ear has a hearing loss sufficiently profound that a normal approximately symmetric hearing condition is incapable of being substantially restored with an amplification adjusted hearing aid and wherein the second ear is capable of hearing sound signals.

12. The hearing aid apparatus of claim 7 wherein the non-audio producing indicator comprises at least one of a light generating indicator and a tactile sensation generating indicator.

13. The hearing aid apparatus of claim 7 wherein the none-audio producing indicator comprises both a light generating indicator and a tactile sensation generating indicator.

14. The hearing aid apparatus of claim 7 wherein the non-audio producing indicator comprises a non-audio producing indicator coupled to at least one of a bracelet, eyeglasses, hearing aid, necklace, watch, ring, anklet, belt, hat, and a subcutaneously positionable implant.

15. The hearing aid of claim 14 wherein the non-audio producing indicator comprises a least one of a light generating indicator and a tactile sensation generating indicator.

16. The hearing aid of claim 7 wherein the non-audio producing indicator includes a first indicia generator configured for being positioned on the user's first side for generating non-audio indicia in response to sounds that originate from the user's first side, and a second indicia generator disposed on the user's second side for generating non-audio indicia in response to sounds that originate from the user's second side.

17. The hearing aid of claim 16 wherein the non-audio producing indicator further comprises a third indicia generator configured for being positioned on the user's front side for generating non-audio indicia in response to sounds that originate from in front of the user, and a fourth indicia generator configured for being positioned on the user's back side for generating non-audio indicia in response to sounds that originate from behind the user.

18. The hearing aid of claim 17 wherein the non-audio producing indicator comprises an annular member wearable by the user and including more than four independently actuated indicia generators for generating a plurality of non-audio indicia that are generated from all sides of the user.

19. The hearing aid of claim 18 wherein the annular member comprises at least one of a collar, a belt, an anklet, a chest-mounted member, and a hat.

20. The hearing aid of claim 7 wherein the non-audio indicator member comprises eyeglasses having one of a tactile sensation indicator and visual sensation generating indicator.

21. The hearing aid of claim 20 wherein the non-audio indicator comprises eyeglasses including both a tactile sensation indicator and a visual sensation indicator.

22. The hearing aid of claim 21 wherein the eyeglasses include a first and second nose engaging member and first and second temples wherein the tactile sensation indicator comprises a first side and second side tactile indicia generator placed on at least one of the respective first and second nose engaging member; and the respective first and second temples.

23. The hearing aid of claim 22 wherein the eyeglasses include a first and second lens and the light sensation indicator includes a first light indicia generator disposed on the first lens and a second light indicia generator disposed on the second lens.

24. The hearing aid of claim 23 wherein the first and second tactile indicia generators comprise variable intensity tactile indicia generators and the first and second light indicia generators comprise variable intensity light indicia generators.

25. The hearing aid of claim 20 wherein the eyeglasses include a first and second lens and the light sensation indicator includes a first light indicia generator disposed on the first lens and a second light indicia generator disposed on the second lens.

26. The hearing aid of claim 25 wherein the first and second light indicia generators comprise a plurality of first and second light sources and a controller for varying the intensity of the light generated through varying the number of light sources actuated.

27. The hearing aid of claim 25 wherein each of the first and second light indicia generators comprise a light indicia generator for generating a light display that relates to a direction of origination of a sound, and a light indicia generator for generating a light display that relates to an intensity of a sound.

28. The device for aiding in hearing of claim 7 wherein the non-audio producing indicator member comprises an electrical stimulation indicia generator.

29. The device for aiding in hearing of claim 7 further comprising a plurality of transducers positioned at a plurality of locations in a space for receiving sounds from the plurality of locations, the transducers including transmitters for transmitting electrical signals representative of the sounds, received by the transducers, a signal processor for receiving the transmitted electrical signals and processing the signals wherein the non-audio producing indicators comprise at least a front, first side, second side, and rear positioned indicia generator, and wherein the signal processor transmits the processed signals to the front, first side, second side, and rear positioned indicia generator in a manner that correlates the signal transmitted to one or more of the front, first side, second side, and rear positioned indicia generators with the position of the one or more of the plurality of transducers from which the signal originated.

30. The device for aiding in hearing of claim 7 wherein the non-audio producing indicator member comprises a body having an indicia generator portion for generating a non-audio indicia, and an attaching portion for attaching the body to at least one or a body part, clothing part, or wearable.

31. The device for aiding in hearing of claim 7 wherein the non-audio producing member is configured for being subcutaneously implanted in a user.

32. The device for aiding in hearing of claim 31 wherein the second hearing aid member comprises a cochlear implant device, and the non-audio producing member is coupled to the cochlear implant device.

33. The device for aiding in hearing of claim 7 wherein the non-audio producing member comprises a screen display.

34. The device for aiding in hearing of claim 33 wherein the non-audio producing member screen display comprises a screen display of at least one of a mobile telephone, laptop, notepad, and computing device, the screen display configured for displaying a direction field containing indicia representative of the origin of at least one sound received by the at least two transducers.

35. The device for aiding in hearing of claim 34 wherein screen display is configured for displaying an indicia representative of the intensity of at least one sound received by the at least two transducers.

* * * * *